US005736010A

United States Patent [19]
Hughes et al.

[11] Patent Number: 5,736,010
[45] Date of Patent: Apr. 7, 1998

[54] PAPER STRENGTHENED WITH SOLUBILIZED COLLAGEN AND METHOD

[75] Inventors: Kenneth E. Hughes, Gahanna; David C. Masterson, Grove City; David J. Fink, Shaker Heights; Barbara A. Metz, Baltimore; Gordon E. Pickett, Reynoldsburg; Paul M. Gemmer, Columbus; Richard S. Brody, Worthington, all of Ohio

[73] Assignee: Ranpak Corporation, Concord, Ohio

[21] Appl. No.: 475,486

[22] Filed: Jun. 7, 1995

Related U.S. Application Data

[60] Division of Ser. No. 250,806, May 27, 1994, abandoned, which is a continuation-in-part of Ser. No. 78,932, Jun. 16, 1993, Pat. No. 5,316,942.

[51] Int. Cl.$^6$ .......................... D21H 17/00; D21H 17/22
[52] U.S. Cl. ........................ 162/143; 162/135; 162/151; 162/157.6; 162/174; 162/180; 162/183; 162/184; 162/185; 435/68.1; 435/71.1; 435/184; 435/212; 435/213; 435/273; 530/356
[58] Field of Search ...................... 162/143, 135, 162/151, 157.6, 174, 180, 183, 184, 185; 435/68.1, 71.1, 184, 212, 213, 273; 530/356

[56] References Cited

U.S. PATENT DOCUMENTS

| | | | |
|---|---|---|---|
| 1,184,518 | 5/1916 | Clapp . | |
| 2,352,922 | 7/1944 | Thomas et al. | 92/21 |
| 2,637,321 | 9/1953 | Cresswell | 128/335.5 |
| 2,934,446 | 4/1960 | Highberger et al. | 106/155 |
| 2,934,447 | 4/1960 | Highberger et al. | 106/155 |
| 3,223,551 | 12/1965 | Tu | 117/140 |
| 3,314,861 | 4/1967 | Fujii | 195/6 |
| 3,532,593 | 10/1970 | Young | 162/2 |
| 3,592,925 | 7/1971 | Evans et al. | 424/119 |
| 3,616,205 | 10/1971 | Ito et al. | 195/6 |
| 3,907,779 | 9/1975 | DeBoer et al. | 260/211.5 R |
| 4,066,083 | 1/1978 | Ries | 128/325 |
| 4,140,537 | 2/1979 | Luck et al. | 106/155 |
| 4,220,724 | 9/1980 | Berg et al. | 435/273 |
| 4,233,360 | 11/1980 | Luck et al. | 428/310 |
| 4,293,647 | 10/1981 | Monsheimer et al. | 435/69 |
| 4,389,487 | 6/1983 | Ries | 435/273 |
| 4,488,911 | 12/1984 | Luck et al. | 106/161 |
| 4,565,580 | 1/1986 | Miyata et al. | 106/124 |
| 4,575,500 | 3/1986 | Burg et al. | 514/121 |
| 4,655,980 | 4/1987 | Chu | 264/102 |
| 4,703,108 | 10/1987 | Silver et al. | 530/356 |
| 4,883,864 | 11/1989 | Schalz | 530/356 |
| 5,021,406 | 6/1991 | Maeda et al. | 54/99 |
| 5,137,875 | 8/1992 | Tsunenaga et al. | 514/21 |
| 5,316,942 | 5/1994 | Fink | 435/273 |

FOREIGN PATENT DOCUMENTS

| | | |
|---|---|---|
| 139458A | 5/1985 | European Pat. Off. . |
| 1145904 | 3/1963 | Germany . |
| 1062083 | 3/1964 | United Kingdom . |
| 2023613 | 1/1980 | United Kingdom . |
| 8103261 | 11/1981 | WIPO . |

OTHER PUBLICATIONS

"Hide Glue for Tub Sizing," TAPPI, pp. 227–228.
"Relationship Between Collagen & Gelatin," pp. 152–153, 164–167, 176–177, 422–425.
"Collagen/Paper Composite Materials for Repulpable/Degradable Packaging & Other Products," Aug. 21, 1991.
Abstract 118126g, "Collagen & Collagen Solutions," Japan Leather Co., Ger. 1,145,904, Mar. 1963.
Hamill et al, "Glue as Beater Sizing," Papaer Trade Journal, 55th year, pp. 32–37.
Calkin, "Modern Pulp & Papermaking," Reinhold Publishing Corp., pp. 269 and 312–313.
The Preparation and Properties Solubilised Collagens; N. T. Crosby et al; J. Soc. Lea. Trades Chemists; 46; 1962; pp. 152–161.
Comminuted Collagen: Estimated Costs of Commercial Production; V.A. Turkot et al; Food Technology; Apr. 1978; pp. 48–57.
The Use of Collagen Dispersions During the Manufacturing of Paper; J.Tkac et al; Kozarstvi 30; 11; 1980; pp. 324–326.
The Science & Technology of Gelatin; Ward, A.G. & Courts, A.; Academic Press; 1977; pp. 152–153, 164–167, 422–425.

Primary Examiner—Herbert J. Lilling
Attorney, Agent, or Firm—Renner, Otto, Boisselle & Sklar

[57] ABSTRACT

A method for making a collagen strengthened cellulosic sheet by providing a cellulosic pulp slurry; adding solubilized collagen to the pulp slurry, and mixing for a time effective for interaction of the cellulosic pulp slurry and solubilized collagen; forming the interacted cellulosic pulp slurry and solubilized collagen into a sheet; and drying the sheet; also, a method for using solubilized collagen for strengthening paper by mixing the solubilized collagen with a cellulosic pulp slurry; and making a cellulosic pulp product from the mixture and drying.

50 Claims, 4 Drawing Sheets

PAPER STRENGTHENED WITH SOLUBILIZED COLLAGEN AND METHOD

This is a divisional of application(s) Ser. No. 08/250,806 filed on May 27, 1994 now abandoned, which is a continuation-in-part application of Ser. No. 08/078,932 filed Jun. 16, 1993, now U.S. Pat. No. 5,316,942.

FIELD OF THE INVENTION

This invention relates to a process for making solubilized collagen and for making solubilized collagen-strengthened paper that provides advantages over other known processes that make improved papers. The invention also relates to the improved solubilized collagen and improved paper made by the process. The invention has utility in making low cost solubilized collagen and in binders for cellulosic products, especially in the production of recycled cellulosic paper that has improved mechanical properties and low cost.

The present invention is related to the application entitled RECYCLE PROCESS FOR THE PRODUCTION OF LOW-COST SOLUBLE COLLAGEN, Ser. No 08/250,803, filed May 27, 1994 and having the same filing date as the present application, the disclosure of which is incorporated by reference herein.

BACKGROUND OF THE INVENTION

The processing of animal hides to produce leather is an ancient art, and today it is a very mature industry. Excellent references to the chemistry of leather manufacture by McLauglin, G. D., et al, *The Chemistry of Leather Manufacture*, Reinhold Publishing Corp, N.Y. (1945), and collagen reactivity by Gustavson, K. H., *The Chemistry and Reactivity of Collagen*, Academic Press Inc., N.Y. (1956), date from the 1940's and 1950's, and are still basic descriptions of the art practiced today. The name "collagen" is derived from the Greek word for glue, as is the term "colloid" which means "gluelike" in Greek.

Skin is composed of four distinct layers, which are, proceeding from outside-in: (1) a thin outer layer of epithelium termed the "epidermis", which is rich in the protein keratin, not collagen; (2) a dense collagen-rich layer, termed the "dermal" or "grain" layer, also called in the older literature the "thermostat" layer; (3) a thicker layer of less-dense, collagen-rich connective tissues, termed the "corium" layer; and (4) an inner layer of "subcutaneous tissue", known to the tanner as "flesh", by which the skin is attached to the underlying tissue.

Although hides may merely be "cured" in salt and/or other biocidal solutions to stop microbial degradation, many hides that are intended for use in leather manufacture are "limed", that is, soaked in a saturated solution of hydrated lime (calcium hydroxide) and water. The liming process initiates the loosening of the epidermis and the subcutaneous layer, and is the first step in the dehairing process. After liming is complete, the hair, epidermis, and any residual flesh, fat and surface muscles are removed by mechanical scraping, and the dermal layer is mechanically cut, along with enough of the corium layer to give the final leather its required thickness, from the remaining inner corium layer.

In leather-making the primary interest is on the dense collagen-rich dermal layer, which is about 25% of the thickness of the corium layer. During the process of leather-making, the dermal tissue receives separate chemical and tanning treatments to stabilize the collagen structure.

The residual portion of the corium layer that is separated from the dermal layer is termed the "limed split" and is a by-product waste of the leather manufacturing process. It is these limed splits that become, for example, the collagen-rich feedstock for sausage casing production, and that have been used as the source of collagen for the examples herein.

During the liming process, the skin imbibes and binds water, and becomes highly swollen; in the process it acquires a very alkaline pH of about 12.5. The chemistry of the liming process is quite well understood. Prior to further leather processing, and in the collagen production process considered here, the skins must be "delimed" by soaking in acid or salt solutions.

Recycling of cellulosic materials to preserve natural resources and reduce costs is presently a desirable environmental objective. The recycled cellulosic materials are preferably used to replace end products where virgin cellulosic materials have historically been used. Unfortunately, products made from recycled cellulosic materials usually have physical characteristics that differ from those made from virgin materials. One of these important characteristics is strength which is often significantly reduced.

Previous attempts to provide increased strength to paper include that disclosed in the patent to Young, U.S. Pat. No. 3,532,593. Young describes a mechanical method for isolating preexisting gelled collagen fibers, not an enzymatic method for solubilizing the collagen as in the present invention. This patent describes a method for removing fat from collagen. The collagen is mechanically treated by beating in an acid solution but remains insoluble. The insoluble mechanically treated collagen was then combined with cellulose beaten pulp and made into paper sheets.

A French journal article by G. Sauret et al, Le collagne ans la fabrication du papier, Revue A.T.P.I., Vol 33, No. 8, October 1979, pp 374–365, discloses a mechanical method using a Turmix-Waring blender for preparing collagen. The mechanically treated collagen is insoluble. It is combined with cellulose pulp and made into paper sheets.

In contrast, the present invention uses a method that combines small amounts of soluble collagen with cellulosic material as further described herein.

SUMMARY OF THE INVENTION

A typical embodiment of the invention is a method for producing an aqueous solution of solubilized collagen by the steps of (a) providing an aqueous ground slurry of insoluble collagen and adjusting the pH of the slurry to obtain activity for a later added proteolytic enzyme; (b) adding the proteolytic enzyme to the pH adjusted slurry; (c) reacting the slurry and enzyme of step b and/or recycled insoluble collagen and enzyme of step e at a temperature, T, and for a time, t, effective for forming a solution increased in solubilized collagen; (d) adding additional water and insoluble collagen to the solution of step (c) and mixing; (e) separating at least some of the solution of step d containing solubilized collagen from the insoluble collagen, whereby at least a portion of the insoluble collagen and proteolytic enzyme is recycled to step c, and a separated solution containing solubilized collagen is withdrawn as product. Another typical embodiment does not employ the recycle step but uses the solubilized collagen directly without removal of enzyme. Typically step c may be repeated two, three, four or more times. Additional enzyme may be added to the recycled insoluble collagen from step e that substantially replaces enzyme removed with the withdrawal product or when the rate of reaction on recycling decreases below a predetermined level. In one typical embodiment, the method is operated as a continuous process.

The reaction may typically be stopped by adjusting the pH to that where the proteolytic enzyme is substantially inactive; and/or by reducing the temperature to that where the proteolytic enzyme is substantially inactive. In another typical embodiment in step a, the liquid or solids content of the wet ground slurry is preferably adjusted so that the solids are at a concentration of about 0.1 to about 1.0 wt %; in step c the temperature, T, is preferably about 5° C. to about 30° C., and more preferably about 15° C. to about 28° C. In another preferred embodiment the solids concentration is between about 0.3 to 0.35 wt % and the reaction of step c is at a temperature of about 10° to about 30° C., and for a time of 10 to 72 hours; more preferably the temperature is between 15° C. and 28° C. Typical proteolytic enzymes are selected from the group consisting of porcine mucosal pepsin, bromelain, chymopapain, chymotrypsin, collagenase, ficin, papain, peptidase, proteinase A, proteinase K, trypsin, microbial protease, and combinations of such enzymes. More preferably the proteolytic enzyme is pepsin or a microbial acid protease. When porcine mucosal pepsin is selected the pH is preferably about 1.5–3.0, and the temperature about 15° C. to about 28° C. Typically, at least 80 wt % of the insoluble collagen is converted to soluble collagen with a number average molecular weight 300,000 daltons and above; while more preferably at least 90 wt % of the insoluble collagen is converted to soluble collagen and the number average molecular weight is above 1,000,000 daltons.

A further typical embodiment of the invention includes a method for producing an aqueous solution of solubilized collagen by the steps of (a) providing an aqueous ground slurry of insoluble collagen; (b) adjusting the water or solid content of the wet ground slurry whereby the insoluble collagen is at a concentration that promotes substantially maximum solubilized collagen concentration in a final product; (c) adjusting the pH of the slurry from step b to obtain activity for a proteolytic enzyme added in step d; (d) adding and mixing the proteolytic enzyme with the pH adjusted slurry; (e) reacting the slurry of step d and/or the recycled insoluble collagen of step g at a temperature, T, and for a time, t, effective for forming a solution comprising solubilized collagen derived from the insoluble collagen particles; (f) adding additional water and insoluble collagen to the solution containing solubilized collagen in step e and mixing; (g) separating at least some of the solution of step f containing solubilized collagen from the insoluble collagen and returning the insoluble collagen to step e, whereby at least a portion of the proteolytic enzyme is recycled, and a separated solution containing solubilized collagen is withdrawn as product. Another typical embodiment does not employ the recycle step but uses the solubilized collagen directly without removal of enzyme. Typically step e may be repeated two, three, four or more times. Additional enzyme may be added to the recycled insoluble collagen from step e that substantially replaces enzyme removed with the withdrawal of product or when the rate of reaction on recycling decreases below a predetermined level. In one typical embodiment, the method is operated as a continuous process. The reaction may typically be stopped by adjusting the pH to that where the proteolytic enzyme is substantially inactive; and/or by reducing the temperature to that where the proteolytic enzyme is substantially inactive. In another typical embodiment in step b, the liquid or solids content of the wet ground slurry is preferably adjusted so that the solids are at a concentration of about 0.1 to about 1.0 wt %; in step e the temperature, T, is preferably about 5° C. to about 30° C., and more preferably about 15° C. to about 280° C. In another preferred embodiment the solids concentration is between about 0.3 to 0.35 wt % and the reaction of step e is at a temperature of about 10° to about 30° C., and for a time of 10 to 72 hours; more preferably the temperature is between 15° C. and 28° C. Typical proteolytic enzymes are selected from the group consisting of porcine mucosal pepsin, bromelain, chymopapain, chymotrypsin, collagenase, ficin, papain, peptidase, proteinase A, proteinase K, trypsin, microbial protease, and combinations of such enzymes. More preferably the proteolytic enzyme is pepsin or a microbial acid protease. When porcine mucosal pepsin is selected the pH is preferably about 1.5–3.0, and the temperature about 15° C. to about 28° C.

Typically, at least 80 wt % of the insoluble collagen is converted to soluble collagen and the number average molecular weight is above 300,000 daltons; while more preferably at least 90 wt % of the insoluble collagen is converted to soluble collagen.

Another embodiment of the invention is a method for producing an aqueous solution of solubilized collagen by the steps of providing an aqueous ground slurry of insoluble collagen; adjusting the water or solid content of the wet ground slurry whereby the insoluble collagen is at a concentration that promotes substantially maximum solubilized collagen concentration that is adapted to strengthen paper in a final product; adjusting the pH of the slurry from Step b to obtain activity for a proteolytic enzyme added in Step d; adding the proteolytic enzyme to the pH adjusted slurry and reacting at a temperature, T, and for a time, t, effective for forming solubilized collagen from the insoluble collagen particles; controlling the reaction conditions for obtaining a high concentration of soluble collagen by measuring the concentration of solubilized collagen and the molecular weight of the solubilized collagen, whereby the reaction is complete when the number average molecular weight fraction above 300,000 daltons and the concentration are substantially maximized; and withdrawing the aqueous solution of solubilized collagen as product.

Feed material for the process can typically come from a variety of sources as long as the feed is relatively clean and has collagen containing material of relatively small particle size, see for example the method of Komanowsky et al discussed below. One typical method for preparing the feed material of a wet ground slurry of insoluble collagen from animal tissues includes the steps: (a) providing soft animal tissues containing collagen; (b) cleaning the collagen containing tissues to remove hair, fat, carbohydrates, and other contaminants; (c) cutting the cleaned collagen containing tissues into small pieces; (d) mixing the small pieces with water to obtain a slurry; (e) adjusting the pH of the slurry substantially near the isoelectric point of collagen from the tissues; (f) wet grinding the resulting pH adjusted slurry to obtain a slurry of insoluble collagen. The pH of this method is typically about 3 to about 7. The invention further encompasses the unique aqueous solutions of solubilized collagen produced by the above methods.

A yet further embodiment of the invention includes a method for making a collagen strengthened cellulosic sheet by the steps of: (a) providing a cellulosic pulp slurry; (b) adding solubilized collagen to the pulp slurry, and mixing for a time effective for interaction of the cellulosic pulp slurry and solubilized collagen; (c) forming interacted cellulosic pulp slurry and solubilized collagen into a sheet; and (d) drying the sheet. Typically the formed sheet may be a sheet such as paper. Another embodiment includes a method for using solubilized collagen for strengthening paper by mixing the solubilized collagen with a cellulosic pulp slurry, molding the mixture and drying.

A still further embodiment includes a strengthened cellulosic pulp composition of a dried reaction product of a mixture of solubilized collagen and cellulosic pulp. Another typical embodiment is a strengthened paper product of paper prepared from a mixture of solubilized collagen and cellulosic pulp.

Yet another typical embodiment includes a method for making a collagen strengthened cellulosic sheet by the steps of: (a) mixing a cellulosic material selected from the group consisting of virgin paper pulp, broke, reclaimed newsprint, reclaimed carton container, or a mixture thereof with a solution comprising water, or water and caustic, and mechanically pulping until a pulp slurry is formed having a consistency of about 3 wt % to about 6 wt % based on dry pulp solids; (b) diluting the pulp slurry to a consistency of about 1 wt % to about 3 wt % based on dry pulp solids and adjusting pH to about 3.5 to about 7.0; (c) adding between about 0.1 dry wt % to about 2 dry wt % soluble collagen (based on dry weight of cellulosic material) to the diluted pulp slurry, and mixing at a shear rate and a time effective for interaction of the diluted pulp slurry solids and soluble collagen, whereby at least a substantial portion of the soluble collagen is bound to the paper pulp to form a collagen-pulp slurry; (d) diluting the collagen-pulp slurry to between about 0.1 dry wt % and 1 dry wt % consistency; (e) forming the collagen-pulp slurry into a sheet and drying the sheet. Typically the mixing in step c is for about 15 minutes. The pH may be adjusted with an acid selected from the group consisting of muriatic acid, HCl, $HNO_3$, $H_2SO_4$, and acetic acid. If desired the method may include the additional step of coating the sheet of step e with sizing prior to drying. Typically the sizing further may be a collagen hydrolyzate having a number average molecular weight of 100,000 daltons or less. The dried sheet may be calendered. Typically the caustic of step a can be a NaOH solution with a concentration of about 0.25 wt % to about 1.00 wt % based on dry weight of cellulosic pulp solids, and a pH range 10-14.

Typically the solubilized collagen has a number average molecular weight above 300,000 daltons, and most preferably above about 1,000,000 daltons. The mixing shear rate and other conditions are adapted to promote collagen-pulp interactions without denaturation of the collagen triple helical structure. In some applications the collagen-paper slurry preferably has a consistency of about 0.5 dry wt %. If desired an alum/rosin additive is added after pulping in step a or after dilution in step b or after refining. Also after forming the sheet in Step e, the formed sheet can be wet pressed to a preselected thickness prior to drying.

In one typical embodiment, when only water is selected in step a, the additional step of refining the pulp/water slurry from Step a is preferred to fibrillate cellulose fibers in order to obtain a selected degree of freeness upon forming a sheet in Step e. When substantially reclaimed newsprint is selected, the degree of freeness is preferably between about 100 CSF and about 150 CSF and when substantially reclaimed carton container is selected the degree of freeness is preferably between about 300 CSF and about 400 CSF.

A yet further embodiment includes the steps of a method for making a collagen strengthened cellulosic sheet by the steps of: (a) mixing a cellulosic material selected from the group consisting of virgin paper pulp, broke, reclaimed newsprint, reclaimed carton container, or a mixture thereof with a solution comprising water, or water and NaOH, and mechanically pulping until a pulp slurry is formed having a consistency of about 3 wt % to about 6 wt % based on dry pulp solids; (b) diluting the pulp slurry to a consistency of about 1 wt % to about 3 wt % based on dry pulp solids and adjusting pH to about 3.5 to about 7.0; (c) adding an alum/rosin additive to the pulp slurry after Step a or to the diluted pulp slurry after Step b; (d) forming the diluted pulp slurry containing alum rosin into a sheet; (e) coating one or both sides of the sheet with collagen hydrolyzate having a number average molecular weight of 100,000 daltons or less; and drying the sheet.

Another typical embodiment includes a method for making a collagen strengthened cellulosic sheet by the steps of: (a) mixing a cellulosic material selected from the group consisting of virgin paper pulp, broke, reclaimed newsprint, reclaimed carton container, or a mixture thereof with a solution comprising water, or water and NaOH, and mechanically pulping until a pulp slurry is formed having a consistency of about 3 wt % to about 6 wt % based on dry pulp solids; (b) diluting the pulp slurry to a consistency of about 1 wt % to about 3 wt % based on dry pulp solids and adjusting pH to about 3.5 to about 7.0; (c) providing an aqueous ground slurry of insoluble collagen; (d) adjusting the water or solid content of the wet ground slurry whereby the insoluble collagen is at a concentration that promotes substantially maximum solubilized collagen concentration and molecular weight in a final product; (e) adjusting the pH of the slurry from Step d to obtain activity for a proteolytic enzyme added in Step f; (f) adding the proteolytic enzyme to the pH adjusted slurry and reacting at a temperature, T, and for a time, t, effective for forming a solution of high molecular weight solubilized collagen from the insoluble collagen particles; (g) controlling the reaction to obtain a high degree of solubilization of collagen and a molecular weight of the solubilized collagen where the collagen is capable of binding with cellulosic pulp by simultaneously measuring the concentration of solubilized collagen and the molecular weight of the solubilized collagen, whereby the reaction is complete when the molecular weight and the concentration are substantially maximized; (h) adding and insoluble collagen with or without additional water to the solution containing high molecular weight solubilized collagen in Step f and mixing; (i) separating at least some of the solution containing high molecular weight solubilized collagen from the insoluble collagen and returning the insoluble collagen to Step d, whereby at least a portion of the proteolytic enzyme is recycled, and the separated solution containing high molecular weight soluble collagen is withdrawn; (j) adding the separated solution of Step i. comprising between about 0.1 dry wt % to about 2 dry wt % soluble collagen (based on dry weight of cellulosic material) to the diluted pulp slurry, and mixing at a shear rate and a time effective for interaction of the diluted pulp slurry solids and soluble collagen, whereby at least a substantial portion of the soluble collagen is bound to the paper pulp to form a collagen-pulp slurry; (k) diluting the collagen-pulp slurry to between about 0.1 dry wt % and 1 dry wt % consistency; (l) forming the collagen-pulp slurry into a sheet; and drying the sheet.

A still further embodiment includes a method for producing a collagen strengthened sheet by the steps of: (a) providing an aqueous ground slurry insoluble collagen and adjusting the pH of the slurry to obtain activity for a proteolytic enzyme added in Step b; (b) adding the proteolytic enzyme to the pH adjusted slurry; (c) reacting the slurry and enzyme of Step b or Step e at a temperature, T, and for a time, t, effective for forming a solution increased in high molecular weight solubilized collagen; (d) adding insoluble collagen with or without additional water to the solution of Step c and mixing; (e) separating at least some of the solution of Step d containing high molecular weight solubilized collagen from the insoluble collagen, whereby at least a portion of the proteolytic enzyme is recycled to Step c, and the separated solution containing high molecular weight solubilized collagen is withdrawn as product; (f) mixing a cellulosic material selected from the group consisting of virgin paper pulp, broke, reclaimed newsprint, reclaimed carton container, or a mixture thereof with a solution comprising water, or water and caustic, and mechanically pulping until a pulp slurry is formed having a consistency of about 3 to about 6 wt % based on dry pulp solids; (g) diluting the pulp slurry to a consistency of about 1 to about 3 wt % based on dry pulp solids and adjusting pH to about 3.5 to about 7.0; (h) adding soluble collagen from Step e to the diluted pulp slurry in an amount from between about 0.1 to about 2 dry wt % soluble collagen (based on dry weight of cellulosic material), and mixing at a shear rate and a time effective for interaction of the diluted pulp slurry solids and soluble collagen, whereby at least a substantial portion of the soluble collagen is bound to the paper pulp to form a collagen-pulp slurry; (i) diluting the collagen-pulp slurry to between about 0.1 dry wt % and 1 dry wt % consistency; and (j) forming the collagen-pulp slurry into a sheet and drying.

Another typical embodiment includes a method for producing an aqueous solution of high molecular weight solubilized collagen by the steps of: (a) providing an aqueous ground slurry of insoluble collagen; (b) adjusting the water or solid content of the wet ground slurry whereby the insoluble collagen is at a concentration that promotes substantially maximum solubilized collagen concentration and molecular weight in a final product; (c) adjusting the pH of the slurry from Step b to obtain activity for a proteolytic enzyme added in Step d; (d) adding and mixing the proteolytic enzyme with the pH adjusted slurry; (e) reacting the slurry of Step d at a temperature, T, and for a time, t, effective for forming a solution comprising high molecular weight solubilized collagen derived from the insoluble collagen particles; (f) adding additional water and insoluble collagen to the solution containing high molecular weight solubilized collagen in Step e and mixing; (g) separating at least some of the solution of Step f containing high molecular weight solubilized collagen from the insoluble collagen and returning the insoluble collagen to Step e, whereby at least a portion of the proteolytic enzyme is recycled, and the separated solution containing high molecular weight solubilized collagen is withdrawn as product; (h) mixing a cellulosic material selected from the group consisting of virgin paper pulp, broke, reclaimed newsprint, reclaimed carton container, or a mixture thereof with a solution comprising water, or water and NaOH, and mechanically pulping until a pulp slurry is formed having a consistency of about 3 to about 6 wt % based on dry pulp solids; (i) diluting the pulp slurry to a consistency of about 1 to about 3 wt % based on dry pulp solids and adjusting pH to about 3.5 to about 7.0; (j) adding soluble collagen from Step e to the diluted pulp slurry in an amount from between about 0.1 to about 2 dry wt % soluble collagen (based on dry weight of cellulosic material), and mixing at a shear rate and a time effective for interaction of the diluted pulp slurry solids and soluble collagen, whereby at least a substantial portion of the soluble collagen is bound to the paper pulp to form a collagen-pulp slurry; (k) diluting the collagen-pulp slurry to between about 0.1 dry wt % and 1 dry wt % consistency; and (l) forming the collagen-pulp slurry into a sheet and drying.

A further embodiment of the invention includes a method for making a collagen strengthened cellulosic sheet by the steps of: (a) providing a cellulosic pulp slurry; (b) adding solubilized collagen to said pulp slurry whereby said cellulosic pulp and said solubilized collagen have a consistency above about 2 wt %, and mixing for a time effective for interaction of said cellulosic pulp slurry and solubilized collagen and whereby said mixing is at a temperature above about 35° C., or more preferably above 40° C.; (d) forming said interacted cellulosic pulp slurry and solubilized collagen into a sheet; and (e) drying said sheet.

DETAILED DESCRIPTION OF THE INVENTION

Figure 1B:
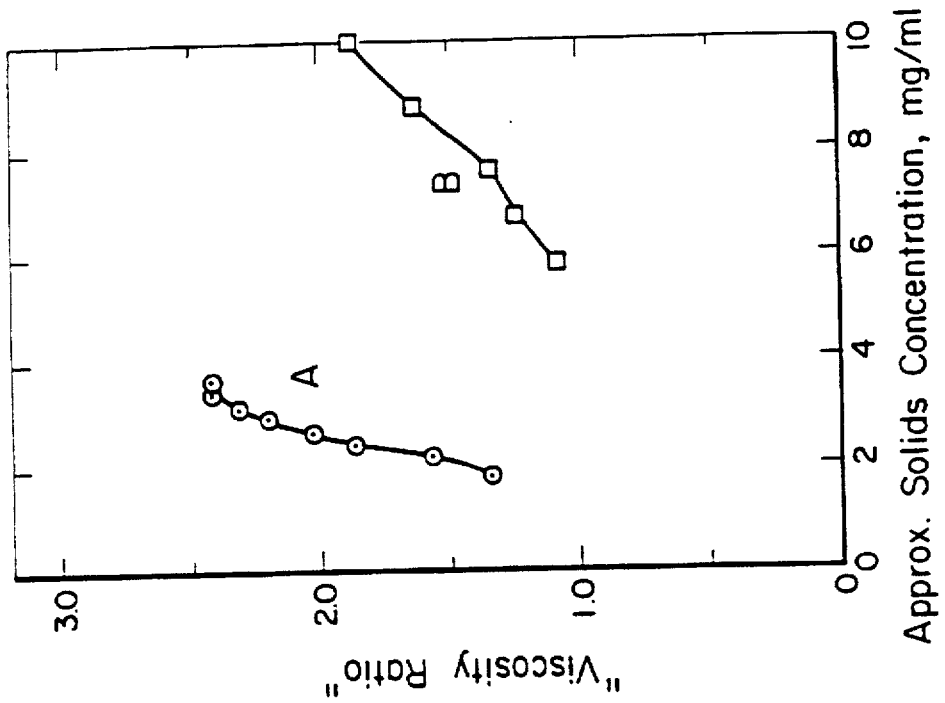
FIG. 1B is a plot showing the ratio of the viscosity determined at 20 rpm to the viscosity at 100 rpm, termed here the "viscosity ratio". The data is calculated from the data in FIG. 1A for both solubilized collagen of the invention (A) or the BA-1 collagen solutions (B). The viscosity ratio is plotted in the ordinate (vertical scale) and the approximate solids concentration, in mg/mL, is plotted in the abscissa (horizontal scale).

It was recognized that solubilized collagen material, added to a cellulose pulp prior to the papermaking process (i.e, mixed with the cellulose pulp fibers in the machine chest), resulted in a significant increase in strength of the paper-collagen composite. This result is surprising since the prior art teaches that larger insoluble aggregates of collagen, such as those produced by mechanical diminution of bovine hides, are necessary. One reason that the use of soluble collagen in papermaking may not have been considered is that soluble collagen can be expected to thermally denature at the fluids temperatures employed in papermaking (greater than about 40° C.). Denatured collagen is not expected to be as useful as native collagen aggregates. It is further surprising since one would expect that the cellulose pulp could best be bound together by larger size particles such as those of the scale of the cellulose pulp itself and not those that are soluble in water. As is demonstrated in the examples herein solubilized collagen that had been centrifuged at very high gravitational forces that would remove substantially all insoluble materials was very effective in increasing the strength of paper. Further, there is no current large-scale use or commercial source for a cost effective collagen solution of this type. Small-scale applications for soluble collagen exist in the food, cosmetic and pharmaceutical industries, for which the products are much higher priced than will be economically acceptable in the cellulose pulp and paper applications of the invention.

Definitions

The following definitions will be useful in reading the disclosure herein:

Acidified collagen—collagen that has been treated with an acid or extracted by an acid solution.

Beating—mixing paper pulp at a relatively high shear rate in order to separate and expand the size of pulp fibers.

Broke—scrap paper from the papermaking process.

Calendering—process of creating surface smoothness and hardness in paper typically by on-line compression between (counter-rotating) cylinders.

Cellulosic pulp—fibers from cellulosic materials that could be wet or dry and produced by mechanical, chemical or other means.

Collagen gel—collagen that exists in its native molecular state in a continuous, highly hydrated fibrillar network.

Collagen sizing—collagen added as a coating after paper sheet has been made.

Degree of freeness—a measure of how easily (freely) water will drain from a paper sheet during production, performed in a standardized test apparatus; one industry recognized standard is Canadian Standard Freeness (CSF).

Mechanically pulping—mechanical separation of cellulosic fibers by specially designed high-shear mixers.

Mechanically working—mechanical shearing of collagen-rich materials to reduce particle size and initiate gel formation.

Mixing collagen and cellulosic (e.g. paper pulp)—mixing is at a relatively lower shear rate (as compared to beating) that is conducive to the reaction of higher molecular weight collagen with cellulosic pulp so as to obtain interaction of solubilized collagen and cellulosic pulp.

Molecular weight—this term as used herein is intended to refer to number average molecular weight unless otherwise specified.

Natural or native collagen—collagen molecules that retain the normal triple-helical assembly of alpha-chains.

Old corrugated container—secondary cellulosic fiber from recycled corrugated container or similar Kraft pulping process sources.

Old newsprint—secondary fiber from recycled newspapers and similar sources.

Reclaimed paper—paper as received from recycling operations.

Recycled paper—reclaimed paper that has been reprocessed and made into new usable paper.

Refining—a pretreatment for the paper pulp that expands and separates cellulosic pulp fibers.

Solubilized collagen—collagen that has been treated to separate the collagen fibrils to render them soluble while retaining the normal triple-helical assembly of native collagen; covalent bonds between collagen fibrils are broken so that smaller collagen molecules can go into solution; this is in comparison to mechanically worked and or acid treated collagen that merely makes the collagen pieces physically smaller but does not break the covalent bonds between fibrils; the solubilized collagen used herein has been solubilized by an enzymatic treatment that breaks the covalent bonds between collagen fibrils.

Viscosity ratio—the ratio of two viscosity measurements of a solution at two different shear rates. This is one typical way to follow the increase or decrease of viscosity due to an increase or decrease of solubilized collagen being produced from a slurry of insoluble collagen. Another typical method would be to use only the viscosity measurement to follow the increase or decrease of solubilized collagen.

A. First General Embodiment

One typical embodiment of the first general embodiment achieves lower costs of operation by utilizing recycle steps to recapture and reuse enzyme that would normally be lost on removal of soluble collagen product solutions. Another typical embodiment of the first general embodiment also has low costs of operation but does not utilize the recycle steps to recapture enzyme. In this latter embodiment the solubilized collagen is sent directly to its end use, such as in papermaking, with no attempt to remove enzyme or otherwise purify the solubilized collagen.

Advantages of the first general embodiment of the invention are in: (1) minimizing the cost of preparing soluble collagen by processing directly from ground skin material to the maximum amount of soluble macromolecules; and (2) at the same time, maximizing the degree of conversion to soluble collagen material capable of binding to cellulosic pulp and controlling the molecular weight of the soluble collagen material in order to enhance the binding effect to the pulp fibers, thereby maximizing the resulting tensile strength and/or other mechanical properties of the paper product. Another major advantage of using solubilized collagen over the insoluble larger aggregates of the prior art, in the production of cellulosic products such as paper, is greater uniformity in the distribution of collagen in the cellulosic pulp.

Bovine skin was selected as the collagen source in the examples described here because collagen preparation methods from skin have been widely reported, and the material is a high volume by-product of the major industries of beef production and leather manufacture; however, it is expected that collagen obtained from other sources (e.g. tendon) will work in the process also.

Collagen solubilization of skin has been accomplished by an enzymatic hydrolysis process with an animal stomach enzyme (e.g. pepsin) and several other enzymes without any other purification steps. The process results in nearly complete solubilization of ground hide preparations in 10–30 hours at room temperature in acidic solutions. Other (untested) enzymes may yield faster or cheaper conversion of collagen-containing tissues, and the process has not necessarily been optimized to minimize enzyme requirements and production time. To date, the process has been scaled to produce approximately 500 gallons of 0.3–0.4% collagen solution, and it has been demonstrated to be relatively easy to control.

EXAMPLES

The following examples, illustrative of the novel compositions and the novel methods of preparing them, are given without any intention that the invention be limited thereto.

Materials

The pepsin used was a crude (relatively unpurified) powder from pig stomach mucosa (Cat. No. P7125) purchased from Sigma Chemical Company, St. Louis, Mo. Lot

070H0437 of this product, used in the examples, contains approximately 15% protein (by UV), with an activity of 91 pepsin units/mg solids and 620 units/mg protein. Residual solids in the preparation appear to be a combination of precipitation salts, buffer salts and/or carbohydrates. Crystallized pepsin has a maximum specific activity of about 3500 units/mg protein.

Additional tests were performed with pepsin, crude powder, from Sigma Chemical Company; AFP 2000, acid fungal protease from a strain of *Aspergillus niger*, from Solvay Enzymes; Newlase A from a strain of *Aspergillus niger*, and Newlase II (from a strain of *Rhizopus niveus*, from Amano Enzyme U.S.A.; Quest AP, quest acid protease from a strain of *Aspergillus niger*, from Quest International; EDC-APA, an EDC acid protease A, and EDC-APB, an EDC acid protease B, from Enzyme Development Corporation.

The collagen slurry used herein for Examples 1A–6A was prepared from ground limed-splits of bovine skin. The collagen was supplied by Teepak's Sandy Run Plant, Columbia, S.C. Typical analyses for the material of Example 6A are pH=6.4; solids content=15.67%; gelatin content =2.62%; fat content=2.1%. A 1974 USDA report by Komanowsky, M., et al, "Production of Comminuted Collagen for Novel Applications", *J. American Leather Chem. Assoc.*, 6, 410–422 (1974), describes techniques for pre-slicing, acidifying and wet-grinding of limed splits to produce five "comminuted" (ground) collagen products, classified by extent of grinding and the resulting particle size and texture. A subsequent 1978 paper by Turkot, et al, "Comminuted Collagen: Estimated Costs of Commercial Production", *Food Tech.*, 48–57 (April, 1978), presents an economic analysis of the production costs for these same five products. The output from this plant closely approximates the ground limed-split material used as a source for collagen in the examples herein.

For Examples 7A to 11A unless otherwise provided the enzymatic collagen solubilization was performed as follows. The collagen source (either ground whole hides or ground limed splits) ground as described in Example 7A with an 0.06 inch cutting head and in a water slurry was spun at 4° C. in a Beckman J2-21Centrifuge (JA-20 rotor) at 10,000 rpm for 20 minutes to remove excess liquid. This centrifuge provided a ratio of rpm to gravitation force of about 1:1, thus at 10,000 rpm the G forces were about 10,000X gravity. The supernatant liquid was removed and the centrifuged solids (7.5 g) were added to a one liter Erlenmeyer flask that contained deionized water (750 mL). The suspension was stirred with a two inch magnetic stir bar and the pH was adjusted using concentrated hydrochloric acid. The enzyme was then added to the flask, which was placed in an incubator set to the desired temperature. Viscosity measurements were made by pouring approximately 100 mL of each reaction mixture into a beaker and bringing to room temperature. The viscosity was measured with a Brookfield Synchro-lectric Viscometer model RVT. Measurements were made at 20 rpm and 100 rpm with spindle No. 3. Three readings were taken at each speed and averaged for the calculation of viscosity in centipoise. Aliquots were removed for viscosity measurements at specified times and then returned to their original flasks.

A collagen solution ("BA-1"), used as a control solution in the examples, was supplied as the soluble skin product, Secolan BA-1, by Kensey Nash Biomaterials, Extort, Pa. The collagen solution is typically a white milky color; pH=3.1–3.3; total solids =1% ±0.2%; active collagen >0.67% (nominally 1% in the examples). This product is sometimes found to be slightly gelled upon receipt. However, based on the pattern observed after electrophoretic analysis, it is believed that the BA-1 is produced by an acid-extraction process, not by an enzymatic reaction as practiced in the present invention.

It was found that the solubilization of collagen-containing solids can be effectively monitored by periodic measurement of the solution viscosity. Fluid viscosities can be conveniently measured by a variety of relatively simple methods, such as the Brookfield Model #RVT Viscometer (#3 Spindle) used with the examples. In this Brookfield system, the force exerted by a fluid upon a disk, which is rotated at constant rotational speed in the fluid, is used to estimate the fluid viscosity. In the collagen solutions described herein, the fluid viscosity will be strongly dependent on the concentration of dissolved collagen, the molecular weight distribution of the soluble collagen and the fluid temperature, and, to a lesser extent, fluid pH and ionic strength.

When the viscosity is independent of the applied force (shear), then the fluid is said to be "Newtonian". For solutions of many macromolecules, including the rod-like collagen molecules considered here, the solution viscosity is very dependent on the force applied to the liquid, and the liquid is said to be "non-Newtonian". When the dissolved macromolecules are highly elongated, and the shear rate (proportional to the rotational speed) is sufficiently high, the molecules tend to orient with the streamlines of the fluid and their effect on the fluid velocity tends to decrease in a manner that is strongly dependent on the shear rate.

Figure 1A:
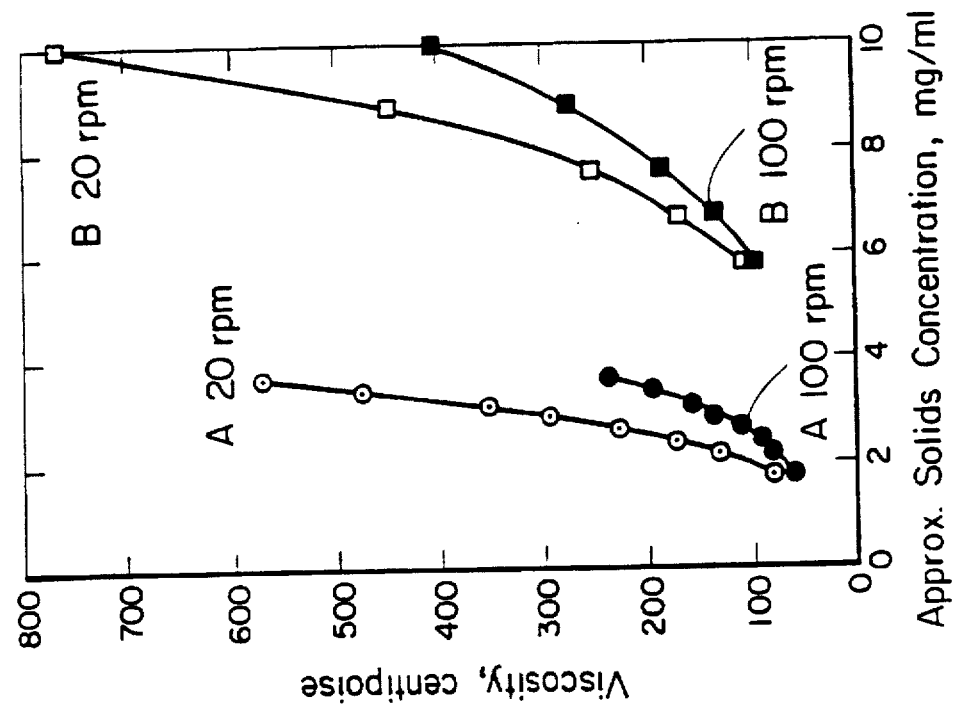
FIG. 1A is a plot showing the non-Newtonian behavior of the collagen solutions. Viscosity of diluted solutions of solubilized collagen of the invention (A) and BA-1 collagen solutions (B) at two shear rates (20 and 100 rpm). Viscosity, in centipoise, is plotted in the ordinate (vertical scale) and the approximate solids concentration, in mg/mL, is plotted in the abscissa (horizontal scale).

The non-Newtonian behavior of collagen solutions is demonstrated in the experiments summarized in FIG. 1A, in which the viscosity of preparations of solubilized collagen and BA-1 were determined at room temperature as the solutions were progressively diluted with distilled water. Some uncorrected increase in solution pH may have occurred in this experiment as the samples were diluted; however, the trend for the data is valid.

For each solution, the viscosity was determined at two rotational speeds, 20 and 100 rpm. The open circles -○- and filled circles -●- represent data for solubilized collagen of the invention at 20 rpm and at 100 rpm, respectively. The open squares -□- and the filled squares -■- represent the data for the BA-1 collagen control at 20 rpm and 100 rpm respectively. Both solutions were more viscous at the lower rotational rate, as expected. The viscosities of the collagen produced in the examples and BA-1 preparations were substantially different, with the produced collagen solution having a much higher viscosity at lower collagen concentrations and a steeper slope. These effects appear to be primarily due to the difference in the average molecular weights of the collagen molecules in the two solutions, with the collagen solution of the invention having the larger number average molecular size. The comparison shows that the method of the invention was successful in making a higher viscosity collagen material at a lower concentration thus showing the number average molecular weight was higher.

The ratio of the viscosity determined at 20 rpm to the viscosity at 100 rpm, termed here the "viscosity ratio", is a convenient measure of this non-Newtonian, molecular-weight-dependent effect. This is illustrated in FIG. 1B, in which the viscosity ratio is higher for collagen solutions of the invention than for BA-1. In FIG. 1B the open circles -○- represent data from the solubilized collagen of the invention and the open squares -□- represent data from the BA-1 collagen solution. The viscosity ratio used herein is a measure of the "degree of conversion" of solid collagen materials to soluble collagen molecules, and also a measure of molecular weight, where higher values of the viscosity ratio will correlate with the desired higher number average molecular weights of the dissolved collagen. In FIG. 1B it is important to note that since the material is being diluted, an increase in viscosity ratio is measuring the increase in concentration of soluble collagen since the molecular weight of the material remains the same. In tests of the examples below, changes in the viscosity and viscosity ratio will be measuring changes in concentration. If desired the peak soluble collagen content can be measured by chromatographic and electrophoretic techniques.

Alternatively, analysis of solubilized collagen composition was routinely performed by SDS polyacrylamide gel electrophoresis (PAGE) that used a 3% stacking gel; 6% running gel, following denaturation by boiling with β-mercaptoethanol. Some irreversible precipitation occurs during the denaturation process. Gels were stained by Coomassie Blue dye and destained in staining buffer only.

PAGE results from this technique demonstrate (results not shown here) that BA-1 solutions contain predominately tropocollagen monomer (300,000 daltons) aggregates. Collagen solutions produced by the present process that had acceptable paper binding properties appeared to have a number average molecular weight of at least 300,000 daltons, with some components having the intact triple helix of alpha, beta and gamma chains as evidenced by PAGE, other preparations may have had a disrupted helix.

Analysis of solubilized collagen composition was also routinely performed by SDS polyacrylamide gel electrophoresis (PAGE) with the Pharmacia PhastGel System. PhastGel Gradient 4–15% polyacrylamide gels were used. The buffer system in the gel is 0.112M Tris acetate, pH 6.4. PhastGel SDS Buffer Strips that contain, at pH 8.1, 0.2M Tricine, 0.2M Tris, and 0.55% SDS were used to run the gels. The separation method was from the PhastSystem Separation Technique File No. 130, Table 2.

Samples were prepared for Gel Electrophoresis by the addition concentrated stock solutions of SDS (20%) and buffers (5 X stock). The final concentrations were 10 mM Tris/HCl (pH 8.0), 1 mM EDTA, 2–2.5% SDS, and 0.01% bromophenol blue. Each sample was then heated at 100° C. for 5 minutes and approximately 1 μl was applied to the gel. In some early experiments, 2-mercaptoethanol (a reducing agent) was added to the sample before heating. The addition of the 2-mercaptoethanol had no effect on the gel pattern.

At the completion of the electrophoresis, the gel(s) were stained with the Pharmacia Silver Kit. The staining method used was from the PhastSystem Silver Kit instruction Manual , Table 2. The Development time and Background Reduction time were doubled for better visibility on the gels.

The SDS detergent in the gels disperses all non-covalent collagen aggregates leaving only covalently joined molecules. The degree to which these molecules migrate on a gel is related to their molecular weights and approximate molecular weights have been assigned to the collagen bands by co-electrophoresis of molecular weight standards on the same gels. PAGE analysis of solubilized collagen indicates bands at ~100,000 daltons (alpha-collagen), ~200,000 daltons (beta-collagen), ~300,000 daltons (gama-collagen), and bands >300,000 daltons. The intensity of the bands is in inverse order of their molecular weights.

Analysis for soluble or insoluble collagen was typically performed by first measuring the amount of hydroxyproline in the sample, then correlating this concentration with the collagen. Hydroxyproline was measured on 0.1 mL samples that were dried in polypropylene tubes at 125° C. The samples were dissolved in 0.05 mL 4M sodium hydroxide, capped, and then autoclaved for 30 minutes. Citric acid (0.05 mL of a 1.4M solution) and chloramine T reagent (1 mL of a solution that contained 1.41 g chloramine T, 10 mL 1-propanol, 10 mL deionized water, and 30 mL of a pH 6 citric acid/acetic acid buffer) were added to each tube which was then incubated for 20 min. at room temperature. PDAB solution (1 mL of a solution that contained 15 g p-dimethylaminobenzaldehyde, 62 mL isopropyl alcohol, and 26 mL 60% perchloric acid) was then added. The samples were incubated at 65° C. for 20 minutes, after which time 0.2 mL of each sample was transferred to a micro-titer plate reader and the absorbance read at 570 um. A sample of purified collagen (Vitrogen 100™; Celtrix) that contained 3.0 mg/mL collagen was found to contain 0.33 mg/mL hydroxyproline. Using this collagen preparation as a standard, multiplication of the hydroxyproline concentration by a factor of 9.1 will yield the collagen concentration.

High pressure liquid chromatography (HPLC) was performed to analyze the intact soluble collagen molecular weight distribution. HPLC was performed with a TOSO-HAAS TSK-GEK G6000PW column (30 cm×7.8 mm) on a Waters 650 Advanced Protein Purification System. Absorbance was monitored at 220 mm with a flow rate of 0.25 mL/Min. (unless noted otherwise). The mobile phase contained 10 mM hydrochloric acid. A column prefilter was used with a 10 um frit.

Eluent fractions containing the HPLC peaks were analyzed by PAGE electrophoresis to determine the size of the constituent collagen molecules. The SDS in the gels disrupts the collagen aggregates so that only the molecular weights of covalently attached molecules can be determined by this method. The first eluting peak (Peak 1) contains molecules with number average molecular weights greater than 300, 000 daltons as well as molecules with number average molecular weights of approximately 200,000 daltons and approximately 100,000 daltons. The smaller molecules appear to be constituents of larger aggregates that were disrupted by the SDS. The second eluting peak (Peak 2) contained molecules with number average molecular weights of approximately 300,000 daltons, approximately 200,000 daltons and approximately 100,000 daltons. The 200,000 dalton and 100,000 dalton molecules appear to be part of 300,000 aggregates that were disrupted by the SDS detergent. The third eluting HPLC peak (Peak 3) contains collagen fragments with number average molecular weights less than approximately 100,000.

In the examples below, it was determined that ground limed splits of beef hide can be nearly completely solubilized when they are subjected to pepsin hydrolysis at pH in the range of 2.0–2.2. Batch reaction times are typically 10–30 hours at room temperature (22°–26° C.). The maximum concentration of soluble collagen typically produced in this process is approximately 0.30–0.40% (3–4 mg dissolved collagen/ml). The process has been demonstrated at up to 2.0 liter-scale and, using essentially the same recipe, at approximately 500-gal scale, as discussed below. Microbial proteases gave similar results as discussed below.

Example 1A

Approximately 15 g of wet Teepak collagen solids were suspended by magnetic stirrer in 750 ml of Columbus, Ohio tap water at room temperature. The solution pH was adjusted to 2.1 with concentrated hydrochloric acid HCl— approximately 65-70 drops. Crude pepsin powder (0.38 g) was then added with stirring into the collagen suspension to initiate the reaction. The suspension was stirred overnight, during which heating of the solution to 26°-27° C. or higher sometimes occurred due to conduction from the stirrer plate. The viscosity of the solution was measured (20 & 100 rpm) periodically during the second day of the reaction until a maximum in the viscosity ratio was achieved, at which time the solution was stabilized by increasing the pH to 3.0-3.5 and/or by placing the solution in the refrigerator. Increasing the pH above 4.0 may initiate irreversible gelation of the collagen solution.

Figure 2:
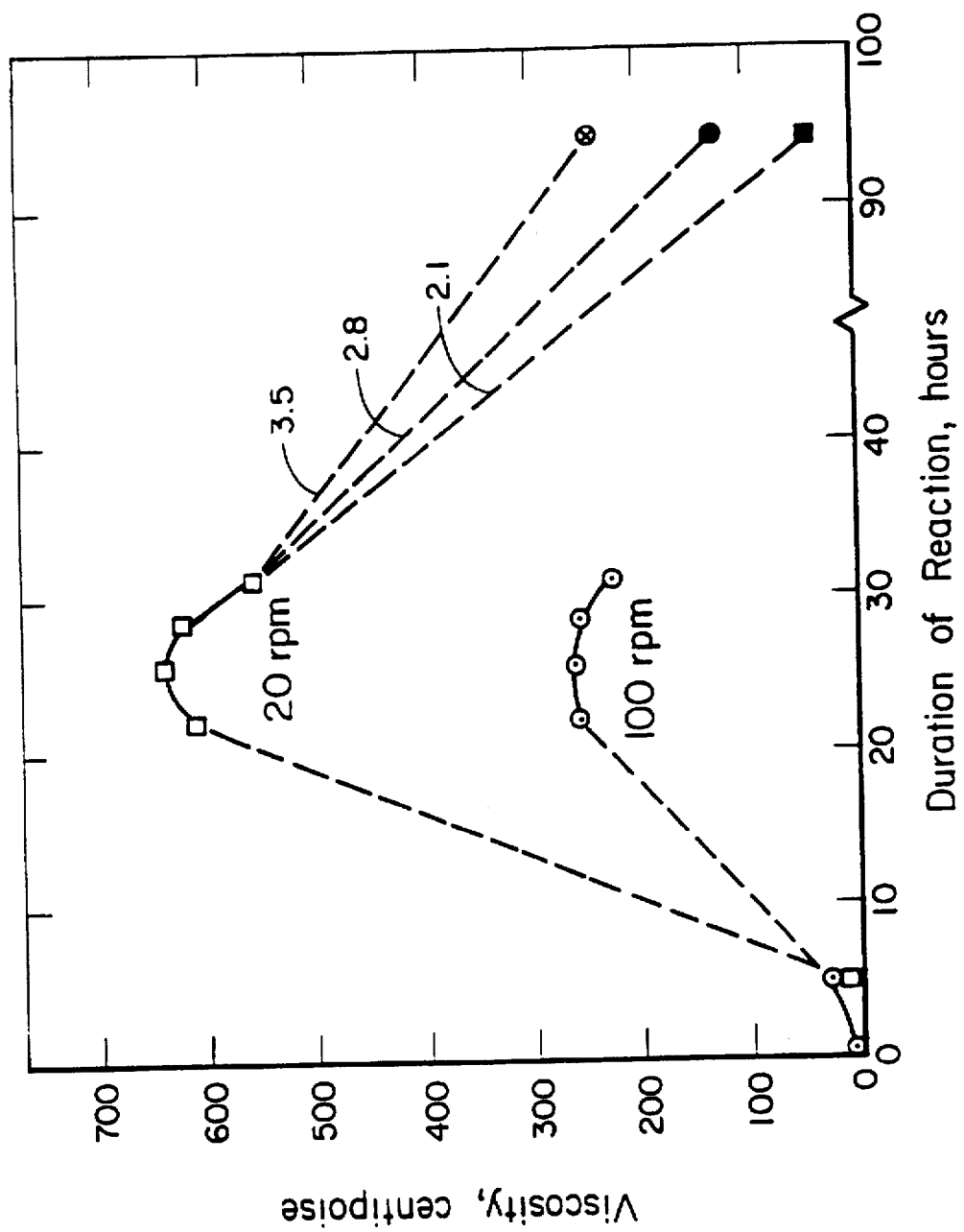
FIG. 2 is a plot of the data for Example 1A showing the viscosity at 20 rpm and 100 rpm. Viscosity, in centipoise, is plotted in the ordinate (vertical scale) and the duration of the reaction, in hours, is plotted in the abscissa (horizontal scale).

Results for Example 1A are plotted in FIG. 2. FIG. 2 shows a plot of viscosity, (in centipoise) as a function of time reaction (in hours). Viscosity measurements were taken at 20 rpm (squares) and 100 rpm (circles). After completion of the reaction at pH 2.1, three samples were taken and the pH adjusted to 2.1 -■-, 2.8 -●-, and 3.5 -⊛-). Viscosity tests at 20 rpm taken several days later confirmed that the samples at pH=3.5 were indeed more stable and retained more of the original viscosity than those at pH=2.1.

Example 2A

Hydrolysis of Teepak collagen at temperatures between 30°-35° C. was investigated in a series of approximately 10 experiments to determine the potential for minimizing pepsin usage in the solubilization process. Typically, enzyme-catalyzed reaction rates will double with every 5°-10° C. increase in temperature. In these experiments, a 4-liter stainless steel beaker was wrapped with heating tape, then insulated with asbestos tape. The solution temperature was controlled by a Variac in line with the heating tape to about ±1°-2° C. The process above was scaled to 2 liters of reaction volume, and a range of lower pepsin concentrations and heating profiles was investigated. In nearly all cases, complete solubilization of the Teepak solids was accomplished in 10-15 hours, and in no case was substantial viscosity developed in the solubilized product.

Typical of the ten experiments is the following: 2 liters of water were added to a beaker, to which was added 40 g of Teepak collagen, then the pH was adjusted to 2.13 with concentrated HCl, and finally 1.0 g crude pepsin was added. Initially the bath temperature was 30.0° C., about 2.5 hours later the temperature was 33° C. and the viscosity at 100 rpm was 19 cps, and about 5.5 hours later the temperature was 36.5° C. with a viscosity of 8 cps. The sample was completely solubilized in less than 8 hours at 33°-36° C. with no increase in viscosity indicating the production of a higher molecular weight material. These experiments demonstrate that it is expected to be more difficult to conserve pepsin in this process by operating at higher reaction temperatures, even early during the hydrolysis process. The maximum feasible temperature for accumulating this particular large molecular weight collagen appears to be about 30° C.

Example 3A

Figure 3:
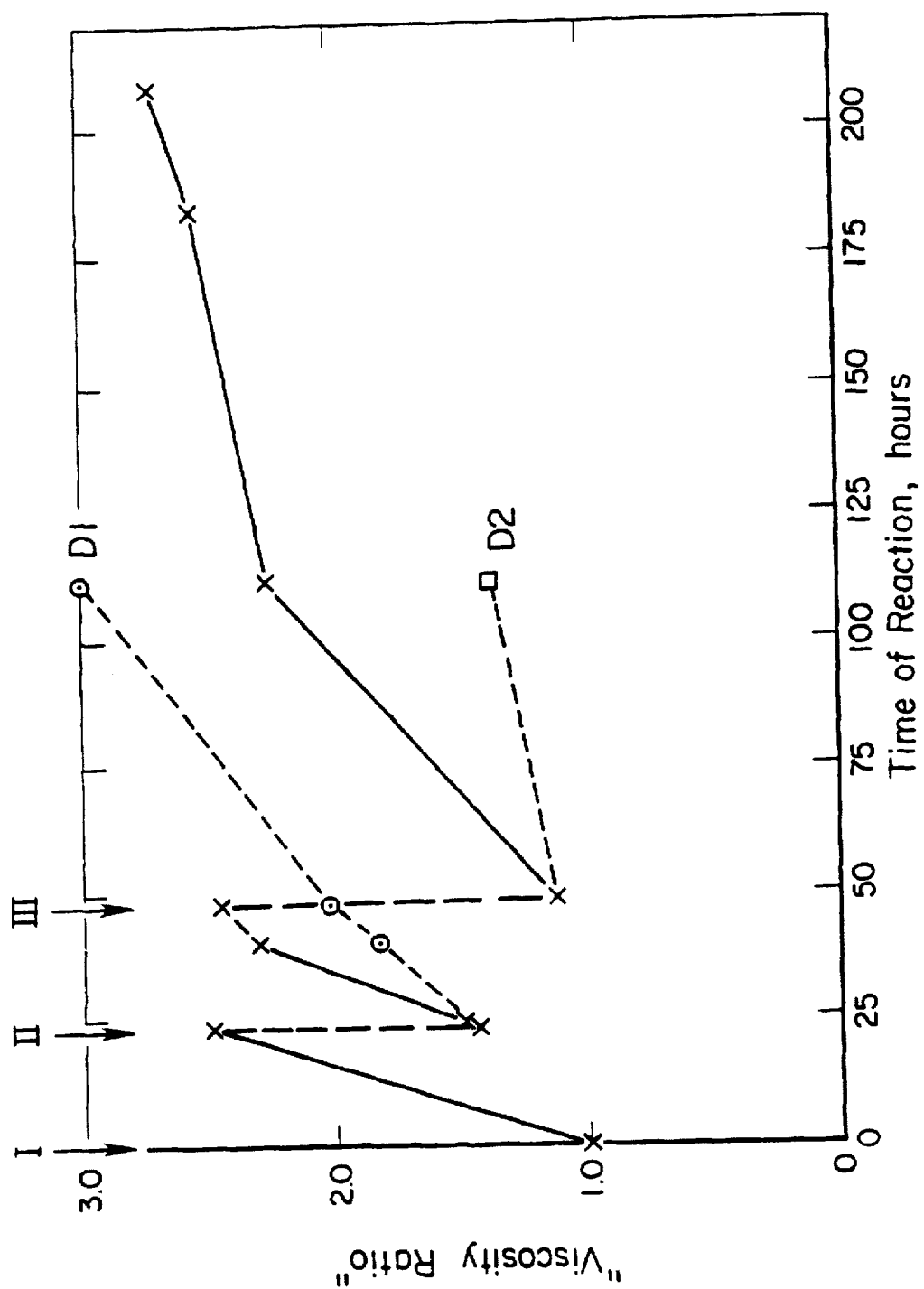
FIG. 3 is a plot of a small-scale batch collagen solubilizing reaction demonstrating the pepsin recycle of Example 3A. The viscosity ratio is plotted in the ordinate (vertical scale) and the time of reaction, in hours, is plotted in the abscissa (horizontal scale).

Another approach for minimizing pepsin usage in the process is illustrated by the experiment summarized in FIG. 3. In this experiment, the recipe above (750 ml Columbus, Ohio tap water, 15.5 g teepak collagen, 0.38 g pepsin, pH=2.1) was mixed on Day 0 to initiate the reaction in a 2-liter flask at room temperature (Roman numeral I). After approximately 1 day, an additional 750 ml of water and another charge of Teepak collagen solids (16.1 g) were added, but no additional pepsin was added to the reactor (Roman numeral II). The flask was stirred for about 5 minutes to mix the contents and the pH was readjusted with 30 drops of concentrated HCl, then the stirrer was turned off and the solids were permitted to settle out. After approximately 30 minutes, 750 ml of supernatant, "Day 1" supernatant (D1), was decanted into another flask, and stirring of both flasks was resumed. The Day 1 Supernatant contained some fine collagen particles, but it contained a much lower suspended solids load than the bottom fraction. The same process of dilution (755 ml water), collagen solids addition (15.2 g Teepak collagen), pH adjustment with 30 drops concentrated HCl (Roman numeral III), and supernatant decanting of "Day 2" supernatant (D2) was repeated in the first flask after approximately 2 days of reaction.

The progression of the hydrolysis reaction is illustrated by the solid lines (-x-) in FIG. 3. The circles -o- show a plot of the progression hydrolysis reaction of the Day 1 supernatant while the squares -□- show a plot of the Day 2 supernatant. In this example three typical charges of Teepak collagen were hydrolyzed by a single charge of pepsin, although the rate of hydrolysis appears to be decreasing with each cycle. Because the viscosity ratios of both the Day 1 and Day 2 supernatants appeared to increase after they were decanted from the main reactor, it was apparent that some pepsin and insoluble collagen was transported along with the supernatant. However, it appears that the pepsin has a higher affinity for solid collagen particles than for soluble collagen, thus most of the enzyme can be recycled several times before it is removed from the system, thereby minimizing the cost of this reagent. Preferably better separation of liquid and solids is obtained if the supernatant is separated from the insoluble collagen by centrifugation.

Most preferably a steady state in the processing recycle steps is desired. This is achieved by adding additional enzyme after the product removal step, when the rate of reaction in the recycle steps decreases below a predetermined level. Most preferably, additional enzyme is added that just replaces that lost with the removal of product.

Example 4A

An experiment was conducted in which 750 ml whitewater (recycle water from a papermaking process) was substituted for the tap water in the standard recipe of Example 3A above. Then 15.5 g Teepak collagen were added, the pH was adjusted to 2.14 with 40 drops of concentrated HCl, and 0.375 g of pepsin were added. Because the room temperature was elevated during this experiment, the reaction was conducted at 29°-31° C., and the solubilization appeared to proceed more quickly than standard reactions at 25°-26° C. In this single reaction, good viscosity was developed, the solids were nearly completely solubilized, and there appeared to be no problem with conducting the process in this solution (see Table 1A). Recycling whitewater from a papermaking process in this way will greatly diminish the amount of water introduced to the process.

TABLE 1A

| | Solubilized Collagen Made in Whitewater From Paper Making | | |
|---|---|---|---|
| Time | Viscosity | | Viscosity |
| (Hours) | 20 rpm | 100 rpm | Ratio |
| 0 | — | — | — |
| 18.5 | 415 | 177 | 2.34 |
| 22 | 440 | 186 | 2.37 |

TABLE 1A-continued

| | Solubilized Collagen Made in Whitewater From Paper Making | | |
|---|---|---|---|
| Time | Viscosity | | Viscosity |
| (Hours) | 20 rpm | 100 rpm | Ratio |
| 26.7 | 365 | 166 | 2.20 |
| 42 | 280 | 136 | 2.06 |

Example 5A

In this example, 500 gal of Savannah, Ga. tap water was delivered to a double-paddle, 600 gal. stainless steel tank, and 75# of Teepak collagen (13.5# solids of @ 18% solids) was dispersed in the water. Approximately 1.4 liters of concentrated HCl was added to bring the pH to 2.14. Pepsin (1.01 kg; Sigma Lot #70H0437) was slowly added, then the tank was covered with polyethylene film and the tank was stirred overnight. After approximately 20 hours, hydrolysis was incomplete (viscosity ratio =1.32). Because the liquid and room temperatures were relatively low (approximately 20° C.), it was decided to attempt to raise the liquid temperature by putting live steam onto the outside bottom of the tank. The steam was used for about 2.5 hours, by which time the liquid temperature was 23° C., the viscosity ratio was 2.15, and the steam heating was discontinued.

At approximately 31 hours, the viscosity ratio was 2.43, which is relatively high for this reaction. It was decided to adjust the pH in the tank to approximately 3.0, by the addition of approximately 450 grams of NaOH flakes, in order to stabilize the solution (slow/stop the pepsin reaction) for use in paper the next day. Approximately 55 gal of the pH=2.1 solution were saved in 5-gal containers prior to the pH adjustment. Because the viscosity ratio dropped slightly overnight for the pH=2.1 solution (open circles, -○- in FIG. 4 and denoted by A) compared to the pH=3.0 solution (closed circles, -●-), it is concluded that pH adjustment is helpful in maintaining the highest possible molecular weight in the product during storage at room temperature.

After approximately 24 hours of reaction, some floating solid material (presumed to be fat because of its low density) was observed on the upper surface of the collagen solution near the mixer shaft. Although no attempt was made in this experiment to remove this residue, it can be easily skimmed from the preparation if the residual fat was found to be detrimental to collagen performance.

Prior to using the collagen solution made in this example and in Example 6A, described below, the solution was filtered by passing it through a knitted plastic screen with openings approximately 1×3 mm, in order to remove a small number of very slowly degrading skin particles. These particles are characteristically the last material to be dissolved by pepsin and can often be found in the 3–5 mm size range. A large sample of these residual particles was filtered from the collagen solution and their dry weight was measured. Based on projecting this sample to the entire batch of collagen solution, it was estimated that more than 95% of the initial solids were solubilized in this process.

Example 6A

Figure 4:
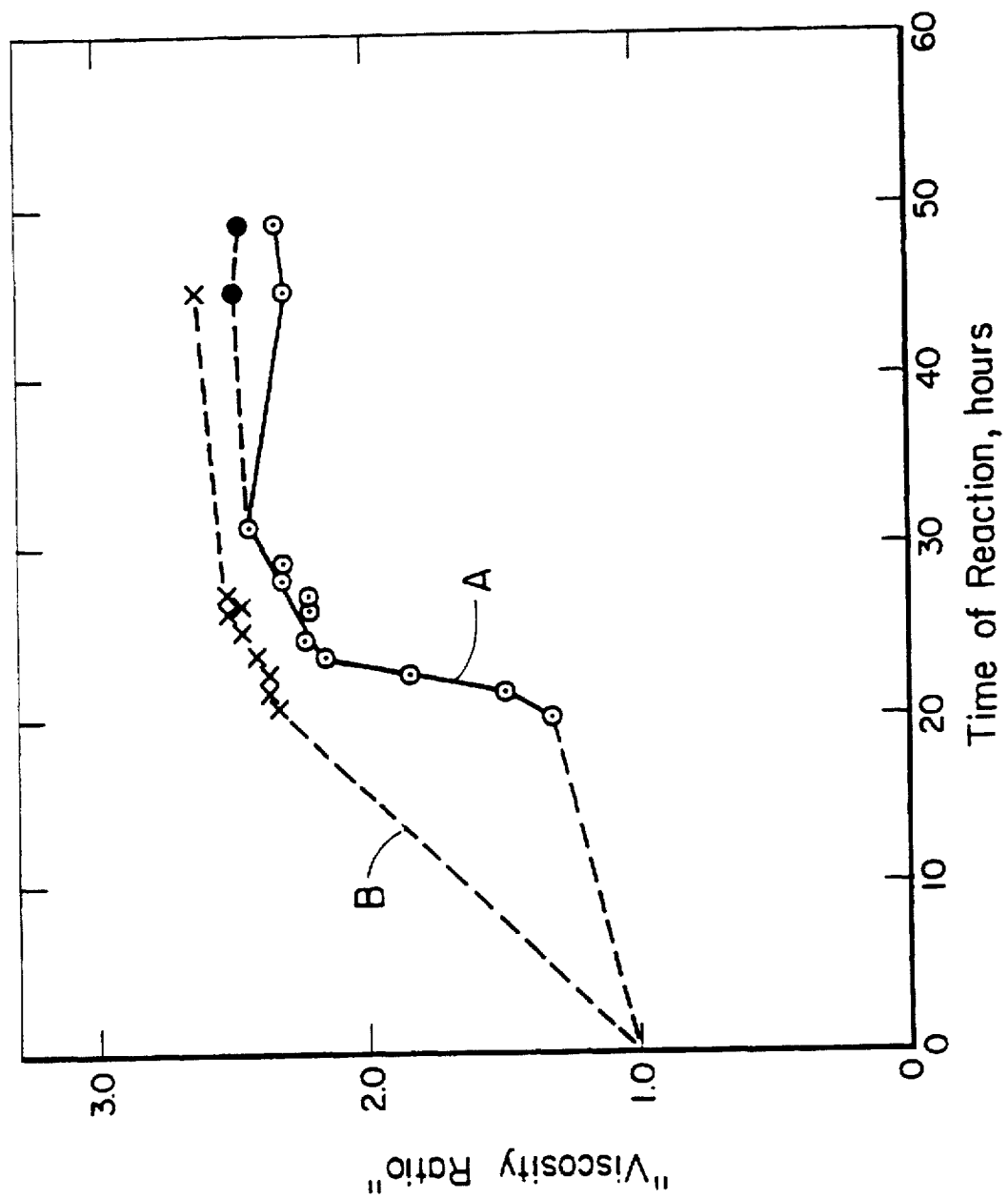
FIG. 4 is a plot of the development of viscosity ratios in Examples 5A (denoted by A) and 6A (denoted by B). The viscosity ratio is plotted in the ordinate (vertical scale) and the time of reaction, in hours, is plotted in the abscissa (horizontal scale).

In this example, the same tank was filled with 500 gal of Savannah, Ga. tap water, which in January was very cold—about 11° C. Teepak collagen (79.5#; 12.5# of solids at 15.67% dry wt.) was dispersed in this water, then 1.5 liters of concentrated HCl was added to bring the pH to 2.18. Pepsin (1.01 kg; Sigma Lot #70H0437) was slowly added, then the tank was covered with polyethylene film. Live steam was placed on the outer bottom of the tank for approximately 4 hours to raise the liquid temperature from 11.5 to 25° C. At this time the pH was 2.40; an additional 0.4 liters of concentrated HCl was added to bring the pH down to 2.29. The tank was draped with polyethylene film to insulate the tank overnight. After approximately 28 hours the viscosity ratio was 2.51, with the temperature at about 22° C. at pH=2.46. Approximately 600 g of flaked NaOH was added to bring the tank contents to pH=2.98, the tank was covered as before and stirred overnight. The final viscosity ratio was 2.61. Results are shown in FIG. 4 at B (-x-).

Since the collagen solution in Example 6A was produced at about a 2°–3° C. higher reaction temperature during the first day than that in Example 5A, the reaction appears to have progressed more rapidly, reaching completion about 4–5 hours sooner. When the pH was adjusted to about 3.0 the final solution appears to have slowed the enzymatic reaction so that little degradation of the soluble product was observed overnight.

The process is intended to produce nearly complete conversion of beef hides to a collagen solution using an enzymatic hydrolysis reaction. Objectives for the process are production of soluble collagen product at the maximum yield, while conversion costs and fixed capital expenditures are minimized. The process is not intended to produce food or medical-grade soluble collagen, and therefore requirements for production of clean solutions are minimal, and no purification of the soluble collagen is anticipated. No attempt has been made to remove the remnants of the other skin components (fat, proteoglycans, other proteins, salts, etc.), which are present in the ground-split feedstock at concentrations lower than collagen.

The process will require a series of cutters and grinders to reduce the feedstock limed splits to a shredded material that can be readily converted to soluble collagen. As cited above, the "front end" of the process will likely look similar to the USDA process for producing comminuted collagen. Depending on the pretreatment of the hides employed to prevent microbial growth, the hides may need to be delimed or acidified to remove residual calcium salts or other biocides. The ground solids are then mixed with process water (perhaps a reduced-solids whitewater stream from a paper plant), the pH is titrated to 2.0–2.2, and enzyme is added to begin the solubilization process. Following conversion, the soluble solids can be pumped directly to a paper making process and mixed with refined pulp solids or stabilized and stored.

In small-scale tests, maximum interaction between collagen and pulp solids appears to result if the pH of the solution is about 4.0 or less and the pulp consistency is 1.0% or lower. Therefore, adjustment of the pulp in the holding tank to about pH 4.0 or less appears to be beneficial although a typical run was at pH 5–6 because the paper was more stable.

Example 7A

"USDA" feed collagen materials were prepared using the method of Komanowsky et al., cited herein, as follows. Two limed splits and one dehaired and limed hide were rolled up and cut to yield 12 inch wide strips. These strips were passed through a strip cutter and then through a rotary knife cutter, An acidic solution was prepared by dissolving 102.15 g of benzoic acid in 1021.5 g of propionic acid. Acidification was carried out in 55 gallon stainless steel tumbling drums by adding 203 lbs of water and 521 g of the above acid solution to the material from the limed hide splits and 235 lb of water and 603 g of acid solution to the whole hide material. The drums were tumbled 15 minutes per hour for four hours. The final pH values were 5.1 and 5.2, respectively. Finally, part of both materials was passed through a 0.06 inch cutting head of the Urschel Comitrol. The remaining part was passed through an 0.200 inch cutting head. The products were poured into small plastic bags and placed into a freezer at −20° C. For later use.

Example 8A

USDA ground limed splits were centrifuged at 4° C. for 20 minutes at 10,000 rpm. The supernatant liquid was removed and the centrifuged limed splits (15 g) were added to a 2 L Erlenmeyer flask that contained deionized water (1500 mL). The suspension was stirred with a magnetic stirrer (2 inch stir bar) and the pH was adjusted to pH 2.1 with concentrated hydrochloric acid. Pepsin (0.76 g) was added to the flask, which was then stirred in an incubator set to 18° C. Aliquots of the reactions (100 mL) were removed at different times and analyzed for viscosity (Table 2A). The pH of each aliquot was adjusted to between pH 3 and pH 3.5 and the samples were stored at 4° C. After the last aliquot was taken (50 hours), analytical samples (0.7 mL) were combined with pH 3.5 acetic acid (1.4 mL) and ultracentrifuged for 1 hour at 45,000 rpm at 4° C. The supernatants and pellets (after being re-suspended in the original volume of buffer) were analyzed for hydroxyproline as shown in Table 2A.

Larger samples of the different fractions (50 mL) were combined with pH 3.5 acetic acid (100 mL) and centrifuged at 20,000 rpm for 4 hours at 4° C. The samples were stored at 4° C. for 9–10 days when they were used to make paper.

TABLE 2A

Summary of Results for Example 8A

| Sample Time (hrs) | Viscosity (20 rpm) (cps) | Hydroxy-Proline in Supernatant (mg/mL) | Hydroxy-Proline in Pellet (mg/mL) | ΔTS (% change from Control with no Addition) |
|---|---|---|---|---|
| 3 | 35 | 0.10 | 0.28 | 15 |
| 7 | 400 | 0.15 | 0.18 | 17 |
| 11 | 1055 | 0.23 | 0.12 | 21 |
| 15 | 1030 | 0.28 | 0.06 | 31 |
| 26 | 800 | 0.29 | 0.05 | 35 |
| 30 | 745 | 0.26 | 0.05 | — |
| 50 | 605 | 0.27 | 0.04 | 27 |

TABLE 2A-continued

This data demonstrates that collagen was increasingly solubilized in this reaction up to approximately 15 hours. This was evidenced by the increase in hydroxyproline in the supernatant, the decrease in the pellet size and hydroxyproline content on centrifugation, and by the initial increase in viscosity. The increase in soluble collagen was correlated with an increase in the tensile strength of the paper to which the collagen was added, where ΔTS represents the % increase in tensile strength above the control paper with no added collagen.

Example 9A

Teepak limed splits were centrifuged at 4° C. for 20 minutes at 10,000 rpm. The supernatant liquid was removed and the centrifuged limed splits (35 g) were added to a 4 L Erlenmeyer flask that contained deionized water (3500 mL). The suspension was stirred with a magnetic stirrer (2 inch stir bar) and the pH was adjusted to pH 2.1 with concentrated hydrochloric acid. Pepsin (1.75 g) was added to the flask, which was then stirred in an incubator set to 20.5° C. Aliquots of the reactions (200 mL) were removed at different times and analyzed for viscosity (Table 2A). The pH of each aliquot was adjusted to between pH 3 and pH 3.5 and the samples were stored at 4° C. until they were used to make paper.

After 27 hours at 20.5° C., one third of the incubated collagen sample was removed and stirred at room temperature. The temperature of the incubator was then adjusted to 30° C. and the remainder of the sample was stirred at this temperature. At specified times, 200 ml samples were removed, the pH adjusted, and the samples store at 4° C. as described above. After the last aliquot was taken, analytical samples (0.7 mL) were combined with pH 3.5 acetic acid (1.4 mL) and ultracentrifuged for 1 hour at 45,000 rpm at 4° C. The supernatants and pellets (after being re-suspended in the original volume of buffer) were analyzed for hydroxyproline content. The supernatants were also analyzed by size exclusion HPLC as shown in Table 3A.

TABLE 3A

Summary of Results for Example 9A

| Incubation Time (hrs) | Peak Area | | | Viscosity (cps at 20 rpm) | Hydroxyproline in Supernatant (mg/mL) | ΔTS° (%) | |
|---|---|---|---|---|---|---|---|
| | Peak 1 ~31 min. | Peak 2 ~34 min. | Peak 3 ~45 min. | | | ONP | OCC |
| 5.5 | 9.0 | 14.9 | 5.7 | 25 | 0.09 | 14 | 27 |
| 21 | 17.5 | 21.0 | 9.5 | 375 | 0.17 | 27 | 42 |
| 23 | 16.4 | 24.7 | 10.1 | 425 | 0.17 | — | —$^f$ |
| 27 | 9.9 | 24.7 | 9.8 | 650 | 0.21 | 28 | 46 |
| 30* | 12.6 | 20.9 | 8.7 | 840 | 0.23 | 32 | 42 |

TABLE 3A-continued

Summary of Results for Example 9A

| Incubation Time (hrs) | Peak Area | | | Viscosity (cps at 20 rpm) | Hydroxyproline in Supernatant (mg/mL) | Δ TS* (%) | |
|---|---|---|---|---|---|---|---|
| | Peak 1 ~31 min. | Peak 2 ~34 min. | Peak 3 ~45 min. | | | ONP | OCC |
| 45.5[b] | 15.9 | 23.4 | 0.7 | 1095 | 0.28 | 37 | — |
| 30[c] | 18.5 | 30.2 | 40.2 | 750 | 0.20 | 26 | 43 |
| 45.5[d] | 18.4 | 24.5 | 54.4 | 45 | 0.30 | 36 | 46 |

[a]This sample was incubated for 27 hours at 20.5° C. and for 3 hours at rt.
[b]This sample was incubated for 27 hours at 20.5° C. and for 18.5 hours at rt.
[c]This sample was incubated for 27 hours at 20.5° C. and for 3 hours at 30° C.
[d]This sample was incubated for 27 hours at 20.5° C. and for 18.5 hours at 30° C.
*ΔTS = % increase in Tensile Strength of paper over control (no collagen) made with 1% soluble collagen added to pulps made from Old New Print (ONP) or Old Corrugated Containers (OCC).
[f](—) indicates analysis not performed.

This data illustrates an increase in soluble collagen throughout the reaction as shown by increases in viscosity and hydroxyproline concentration in the supernatant fraction. The increase in soluble collagen is correlated with an increase in the tensile strength of paper to which the collagen was added. Samples kept at 30° C. after 27 hours of reaction demonstrated progressive conversion of high molecular weight collagen to degradation products (increase in HPLC peak 3), but in this case the lower molecular weight did not result in a similar decrease in tensile strength of papers to which it was added. This latter effect indicated that the collagen has a positive effect on the paper even when some of the material has been digested to relatively low molecular weights. Gel electrophoresis indicates the presence of significant concentrations of approximately 200,000 dalton collagen and approximately 100,000 dalton collagen even after reaction at 30° C. for 18.5 hours. Thus, in the absence of detergent there may be significant amounts of 300,000 or higher molecular weight material. Substantial high molecular weight collagen was present as evidenced by the high areas of HPLC peaks 1 and 2 in samples indicated by footnotes c and d.

Example 10A

Two preparations of solubilized collagen were combined as follows. Each preparation was made from Teepak limed splits that were centrifuged at 4° C. for 20 minutes at 10,000 rpm. The supernatant liquid was removed and the centrifuged limed splits (35 g) were added to a four liter Erlenmeyer flask that contained deionized water (3500 mL). The suspension was stirred with a magnetic stirrer (2 inch stir bar) and the pH was adjusted to pH 2.1 with concentrated hydrochloric acid. Pepsin (1.75 g) was added to the flask, which was then stirred in an incubator set to 19° C. One preparation was incubated for 31.5 hours (final viscosity at 20 rpm was 1160 cps) and the other preparation was incubated for 21 hours (final viscosity at 20 rpm was 1025 cps). The two preparations were stored at 4° C., with no pH adjustment, for 6 days, then one and a half liters of each preparation were combined in a 4 liter flask, stirred to mix, and then rapidly heated to about 30° C. in a water bath. The flask was then stirred in a 32° C. incubator and, at specified times, 200 ml samples were removed, the pH adjusted to between 3.0 and 3.5, and the samples stored at 4° C. The results from this reaction and the results of tensile tests run on papers made with these materials are shown in Table 4A below.

This data demonstrates that, although not all of the collagen was initially soluble (hydroxyproline measurements increased throughout the reaction), there was a rapid decrease in collagen number average molecular weight throughout the course of the 30° C. reaction period as indicated, for example, by the viscosity decrease and increase in HPLC peak 3 area. This decrease in molecular weight did not effect the gain in tensile strength until all of HPLC peak 1 (number average molecular weight >300,000 daltons) and nearly all of HPLC peak 2 (number average molecular weight ~300,000 daltons) were converted to smaller fragments. Gel electrophoresis indicated the presence of a small amount of ~100,000 dalton molecular weight collagen even after 25.5 hours at 32° C. Most of the collagen has been converted to fragments with number average molecular weights less than 100,000 daltons by this time. HPLC analysis of this sample, which is done in the absence of detergent, indicates no peak 1 and a small of peak 2. The remaining 100,000 dalton number average molecular weight fragments seen on the gel presumably aggregate in the absence of detergent to form the 300,000 dalton triple helix seen as HPLC peak 2. It is this triple helical collagen that appears to impart the enhanced properties to the paper.

TABLE 4A

Summary of Results for Example 10A

| Incubation Time (hrs) | Peak Area | | | Viscosity (cps) | Hydroxyproline in Supernatant (mg/mL) | ΔTS (% Change From Control) |
|---|---|---|---|---|---|---|
| | Peak 1 ~31 min. | Peak 2 ~34 min. | Peak 3 ~45 min. | | | |
| 0 | 2.1 | 29.1 | — | 1260 | 0.28 | +48 |
| 2 | 25.8 | 25.6 | 12.5 | 705 | 0.27 | — |
| 3 | 26.8 | 24.9 | 19.3 | 520 | 0.29 | — |

TABLE 4A-continued

Summary of Results for Example 10A

| | Peak Area | | | | Hydroxyproline | ΔTS (% Change |
|---|---|---|---|---|---|---|
| Incubation Time (hrs) | Peak 1 ~31 min. | Peak 2 ~34 min. | Peak 3 ~45 min. | Viscosity (cps) | in Supernatant (mg/mL) | From Control) |
| 4 | 20.4 | 31.1 | 37.2 | 215 | 0.32 | +46 |
| 5 | 18.8 | 28.8 | 46.1 | 165 | 0.29 | — |
| 6 | 19.9 | 31.7 | 65.3 | 75 | 0.34 | +37 |
| 7 | 13.3 | 28.8 | 72.2 | 35 | 0.35 | +41 |
| 8 | 14.7 | 23.8 | 83.9 | 20 | 0.37 | +41 |
| 9 | 10.6 | 22.1 | 93.9 | 15 | 0.37 | +47 |
| 12.5 | 6.5 | 16.7 | 105.5 | 10 | 0.39 | +41 |
| 25.5 | 0 | 5.0 | 127.6 | 5 | 0.38 | +30 |

Example 12A

Reactions of microbial proteases with the collagen from limed splits as described above were as summarized in Tables 5A and 6A:

Microbial proteases were reacted with ground limed splits from two sources at 17° C. A summary of the optimum results with regards to protease concentration and pH is shown in Table 5A.

TABLE 5A

Reaction of Microbial Proteases with Ground Limed Splits

| Enzyme | pH | Maximum Viscosity (20 rpm) | Hrs. to Maximum Viscosity |
|---|---|---|---|
| Newlase II (0.08 g) | 2.6 | 1840 | 18 |
| Quest AP (0.08 g) | 2.6 | 1535 | 22 |
| AFP 2000 (0.08 g) | 2.6 | 1415 | 22 |
| EDC-APA (0.08 g) | 2.5 | 1085 | 18 |

TABLE 6A

Reaction of Microbial Proteases with Teepak Limed Splits

| Enzyme | pH | Maximum Viscosity (20 rpm) | Hrs. to Maximum Viscosity |
|---|---|---|---|
| Newlase II (0.075 g) | 2.6 | 1386 | 19 |
| Quest AP (0.08 g) | 2.6 | 945 | 24 |
| EDC-APA (0.08 g) | 2.5 | 745 | 20 |
| Newlase A (0.04 g) | 2.6 | 665 | 23 |
| AFP 2000 (0.08 G) | 2.6 | 515 | 41 |
| EDC-APB (0.08 g) | 3.0 | 435 | 39 |

All of the microbial proteases produce significantly viscous collagen solutions, demonstrating their use for solubilizing collagen from ground limed splits.

Collagen solutions prepared by the above examples appear to be stable at room temperature for 12–24 hours, and stability can be enhanced by increasing solution pH to 3.0–3.5 and/or by reducing the solution temperature to 5°–10° C.

The process has demonstrated the feasibility of production of a low-cost soluble collagen product by the substantially complete solubilization of beef hide collagen (ground limed-splits). The process can be conducted at near-ambient conditions and is relatively easy to control. Of particular interest is the recycle method that reduces the cost of the relatively expensive proteolytic enzymes.

B. Second General Embodiment

The second general embodiment typically utilizes the solubilized collagen produced in the first general embodiment or if desired solubilized collagen can be obtained from other methods. One major advantage of using the solubilized collagen of the first general embodiment is of course the low cost of the material so produced. This cost factor is a major advantage in the paper making art.

The invention improves the strength of recycled paper, conventional paper, and mixtures thereof. The invention is especially useful in producing recycled paper because recycled paper made from recycled cellulosic fibers is generally weaker than paper made from virgin cellulose fibers. As used herein the feedstocks in the invention typically are: virgin paper pulp which is paper pulp made from nonrecycled materials; broke which is scrap at the papermaking plant; reclaimed newsprint which is recycled newspaper and similar paper; reclaimed corrugated container which is recycled old corrugated container and similar material; similar cellulose based papers; and mixtures thereof.

The invention discloses the use of collagen solubilized with enzymes to improve the strength and other properties of paper type products made from cellulose fibers. Typically the method for making a collagen strengthened paper comprises mixing feedstock with water, or water and caustic (e.g. NaOH), and mechanically pulping until a pulp slurry is formed. Preferably the pulp slurry has a consistency of about 3 to about 6 wt % based on dry pulp solids. The pulp slurry is then diluted to a consistency of about 1 to about 3 wt % based on dry pulp solids and adjusted to a pH of about 3.5 to about 7.0. Between about 0.1 to about 2 dry wt % solubilized collagen is added to the diluted pulp slurry, and the resulting slurry is mixed at a shear rate and a time effective for interaction of the diluted pulp slurry solids and soluble collagen, whereby a substantial portion of the solubilized collagen is bound to the paper pulp to form a collagen-pulp slurry. The collagen-pulp slurry is then diluted, preferably to between about 0.1 and 1 dry wt % consistency, and finally the collagen-pulp slurry is formed into a sheet and dried.

Example 1B

Collagen Solutions as a Coating.

The old newsprint (ONP) or the old corrugated container (OCC) was shredded and soaked in a 1 percent sodium hydroxide solution overnight.

The shredded material was pulped in a Tappi disintegrator for 15 minutes. The pulp was mixed with additional water and a sheet was formed in a Noble and Wood headbox with a Duotex 162-DD-226 forming fabric. The sheet was wet-pressed on the Noble and Wood and then calendered to increase density (blotter paper was used on each side and the gap on the calender rolls was set at 0.76 mils). The sheet was dried on a hot plate surface temperature of about 100° C. under tension for 1 minute. Collagen hydrolysate (MW<2000 daltons) supplied by Secol (Exton, Pa.) or soluble native collagen (MW>300,000 daltons) supplied by Gattefosse' Corp. (Elmsford, N.Y.) were applied to the sheets of recycled paper using either a No. 10 or No. 20 wire-wound rod. The coated sheets were dried either in a forced air oven at 100° F. for 10 minutes or allowed to dry at ambient conditions overnight. The coated sheets were evaluated for basis weight, burst strength, and tensile properties as reported in Table 1B. This table also details amount of pulp and coating weight used.

Gains of tensile strength were observed in all samples tested, ranging from about 125–300 percent over the appropriate control without collagen. While ONP and OCC controls were only approximately 25% as strong as the Kraft paper standard, several coated samples were as strong or stronger than the Kraft standard.

Example 2B

Native Collagen Added to Pulp in Headbox

The ONP or OCC was shredded and soaked in a 1 percent sodium hydroxide solution overnight. The material was pulped in a Tappi disintegrator for 15 minutes. The pulp was put in the headbox of the Nobel and Wood, and water at various temperatures (14–17° C. or 36°–38° C.) was added. The pH of the slurry was 7. Various amounts of native collagen solution (0.3% solids) were added. The slurry was allowed to settle and stand for 4 to 10 minutes. The sheet was formed on a Duotex 162-DD-226 forming fabric. The sheet was wetpressed on the Noble and wood and then calendered to increase density. (Blotter paper was used on each side and the gap on calender rolls was set at 0.762 mm). The sheet was dried on a hot plate for 1 minute. The formed sheets were evaluated for basis weight, burst strength, and tensile properties as reported in Table 2B. This table also details the amount of pulp and collagen additive used. Gains of tensile strength were observed in all samples tested, ranging from about 140–350% over the appropriate control without solubilized collagen. While ONP and OCC controls were approximately 25% as strong as the Kraft paper standard, several samples were stronger than the Kraft standard. No correlation was observed between the amount of collagen added and the tensile strength improvement.

TABLE 1B

Collagen Applied as a Coating

| | | | | | | Physical Characteristics | | | Tensile Properties | | |
|---|---|---|---|---|---|---|---|---|---|---|---|
| | Sheet Composition | | | | | Basis | Mullen Burst | | | | % Change |
| Sample No. | Gms. Fiber | Fiber | Collagen Solution/% | Rod | Drying Technique | Weight kg/279 m² | Strength MPa | Caliper mm | TS/BW | TS MPa | from Control |
| CC-1 | 5.5 | Kraft | None | — | — | 13.1 | .159 | .11 | 1.30 | 17.02 | — |
| CC-2 | 5.5 | ONP | None | — | — | 12.5 | .034 | .18 | 0.33 | 4.08 | — |
| CC-4 | 5.5 | ONP | Hydrolysate | 20 | oven | 17.6 | .108 | .13 | 1.27 | 22.34 | +289 |
| CC-5 | 5.5 | ONP | " | 20 | air | 17.1 | .109 | .13 | 1.06 | 18.20 | +151 |
| CC-6 | 5.5 | ONP | " | 10 | air | 15.3 | .092 | .12 | 1.32 | 20.24 | +304 |
| CC-7 | 5.5 | ONP | " | 10 | oven | 16.8 | .108 | .13 | 1.15 | 19.38 | +253 |
| CC-8 | 5.5 | ONP | Native | 10 | air | 13.3 | .102 | .11 | 1.11 | 14.71 | +238 |
| CC-9 | 5.5 | ONP | " | 10 | oven | 14.0 | .109 | .12 | 1.02 | 14.22 | +211 |
| CC-10 | 5.5 | ONP | " | 20 | air | 14.4 | .112 | .12 | 1.09 | 15.76 | +235 |
| CC-11 | 5.5 | ONP | " | 20 | oven | 13.8 | .098 | .12 | 1.10 | 15.22 | +238 |
| CC-12 | 4.5 | OCC | None | — | — | 14.4 | .055 | .19 | 0.38 | 5.50 | — |
| CC-14 | 4.5 | OCC | Hydrolysate | 20 | oven | 18.2 | .178 | .14 | 1.47 | 26.68 | +283 |
| CC-15 | 4.5 | OCC | " | 20 | air | 18.8 | .137 | .15 | 1.09 | 20.45 | +185 |
| CC-16 | 4.5 | OCC | " | 10 | air | 17.7 | .161 | .14 | 1.47 | 25.98 | +284 |
| CC-17 | 4.5 | OCC | " | 10 | oven | 17.2 | .161 | .13 | 1.54 | 26.41 | +302 |
| CC-18 | 4.5 | OCC | Native | 10 | air | 13.8 | .124 | .12 | 1.02 | 14.01 | +166 |
| CC-19 | 4.5 | OCC | " | 10 | oven | 13.8 | .13 | .12 | 1.12 | 15.5 | +194 |
| CC-20 | 4.5 | OCC | " | 20 | air | 14.0 | .12 | .13 | 0.86 | 12.1 | +126 |
| CC-21 | 4.5 | OCC | " | 20 | oven | 14.0 | .13 | .13 | 0.93 | 13.0 | +146 |

TABLE 2B

Collagen Added to Pulp

| | Sheet Composition | | | | Physical Characteristics | | | Tensile Properties | | |
|---|---|---|---|---|---|---|---|---|---|---|
| Sample No.[a] | Gms. Fiber | Fiber | Native Collagen Added % | Headbox Time | Slurry Temp. °C. | Basis Weight kg/279 m² | Mullen Burst Strength MPa | Caliper mm | TS/BW | TS MPa | % Change from Control |
| CP-1  | 5.5 | Kraft | —  | —  | —    | 13.1 | .159 | .11 | 1.30 | 16.97 | —    |
| CP-2  | 5.5 | ONP   | —  | —  | —    | 12.5 | .034 | .18 | 0.33 | 4.07  | —    |
| CP-5  | 5.5 | ONP   | 1  | 4  | 17.1 | 14.3 | .092 | .13 | 1.11 | 15.82 | +240 |
| CP-6  | 5.5 | ONP   | 1  | 4  | 35.9 | 13.1 | .071 | .12 | 1.01 | 13.19 | +210 |
| CP-7  | 5.5 | ONP   | 2  | 4  | 15.4 | 13.3 | .103 | .11 | 1.48 | 19.70 | +353 |
| CP-8  | 5.5 | ONP   | 2  | 4  | 15.4 | 13.9 | .081 | .12 | 0.98 | 13.62 | +201 |
| CP-9  | 5.5 | ONP   | 1  | 10 | 37.6 | 13.2 | .089 | .12 | 1.08 | 14.20 | +231 |
| CP-10 | 5.5 | ONP   | 10 | 10 | 35.7 | 16.2 | .110 | .14 | 1.07 | 17.33 | +227 |
| CP-11 | 4.5 | OCC   | —  | —  | —    | 14.4 | .055 | .19 | 0.38 | 5.48  | —    |
| CP-14 | 4.5 | OCC   | 1  | 4  | 14.5 | 13.0 | .132 | .11 | 1.48 | 19.24 | +289 |
| CP-15 | 4.5 | OCC   | 1  | 4  | 38.3 | 13.5 | .111 | .12 | 0.90 | 12.18 | +138 |
| CP-16 | 4.5 | OCC   | 2  | 4  | 14.9 | 13.2 | .146 | .11 | 1.79 | 23.68 | +371 |
| CP-17 | 4.5 | OCC   | 2  | 4  | 37.1 | 12.4 | .089 | .11 | 1.06 | 13.13 | +179 |
| CP-18 | 4.5 | OCC   | 1  | 10 | 35.3 | 12.7 | .096 | .11 | 1.10 | 13.91 | +189 |

[a]All samples except CP-1 were soaked in NaOH.

Example 3B

The examples below illustrate: (1) fiber stocks prepared from old corrugated containers (OCC) and old newsprint (ONP); (2) the addition of 1% solubilized collagen to those stocks either before or after the paper sheet is formed. The feedstocks were used to prepare a lightweight, 13.6 kg/279 m², basis weight paper. Some stocks were treated with caustic soda at ambient water temperature. Solubilized collagen was added to the stock chest before paper production in the ratio of 1% of the dry pulp solids, and mixed for at least 15 min. at a temperature of less than 39° C. The papers were produced as follows:

A. Materials
 1. Solubilized collagen prepared as in Example 5A.
 2. Post consumer old newsprint (ONP).
 3. Liner board (rolls) used as old corrugated container (OCC) did not contain corrugated medium—Stone Container, Savannah, Ga. The pulped material is, however, the as if corrugated materials had been used.
 4. Concentrated HCL (31%).

B. Equipment:
 1. Black Clawson 2.4 m HCVY Hydrapulper 61 cm bottom Vokes rotor and drive assembly—7570 liter capacity.
 2. Sprout-Waldron 30 cm Twin-Flow refiner—1770 rpm equipped with plates D5B053 motor end and D5B054 control end.
 3. Sandy Hill Corporation manufactured (1967) Fourdrinier type paper machine with a 97 cm wire width. The table has a forming length of 44.3 meters. The slice width is 84 cm and the machine was operated with edge curls. The machine's press section consisted of two presses, the first one being a straight through double felted and the second being a bottom-felted reversed press. Each press nip is limited to 2.06 MPa. The bottom press rolls have rubber venta nip covers. The top roll in the second press has a stonite cover. The machine's dryer section consists of two banks of 91 cm diameter dryer cans, seven cans in the first section and five cans in the second section. Between the dryer sections is a size press arrangement which can be operated as a horizontal or a vertical unit. With proper rolls installed, the unit can also be used as a breaker stack. Following the second dryer section is an eight roll, seven nip calender stack. Rolls up to 102 cm in diameter can be wound on the reel.

C. Paper stock:
 100% OCC/530 kg (Oven Dried)
 Old corrugated container was dispersed in ambient temperature water using pulper No. 1. The dispersed old corrugated container stock was pumped to a 26,500 liter refiner chest and refined from 644 Canadian standard freeness (CSF) to 325 CSF in 145 minutes.
 100% ONP/552 kg (Oven Dried)
 Old newsprint was dispersed in 66° C. water using pulper No. 1. The dispersed old newsprint stock was pumped to a 26,500 liter refiner chest and refined from 135 CSF to 107 CSF in 30 minutes.
 100% OCC/854 kg (Oven Dried)
 1. Dispersed old corrugated container in ambient temperature water using pulper No. 1.
 2. Pumped dispersed stock to 26,500 liter refiner chest.
 3. Refined stock from 638 CSF to 353 CSF in 200 minutes.
 100% ONP/871 kg (oven dried)
 1. Dispersed ONP in 66° C. temperature water using pulper No. 1.
 2. Pumped dispersed stock to 7000 gallon refiner chest.
 3. Refined stock from 119 CSF to 99 CSF in 42 minutes.

D. Paper Machine Operations:
 Stock from the paper machine chest was pumped via a Fischer-Porter flow controller to the suction side of a fan pump. The thick stock was then diluted with white water to operate the stock flow system. Production rate on the machine was controlled by the amount of the thick stock flowing into the fan pump. The stock was then pumped through an explosion chamber manifold into the primary headbox. The headbox was operated under vacuum with a top holey roll. Machine speed was approximately 175 ft/min. resulting in a paper throughput of about 300 lbs./hr.

Wire Set-Up

The forming fabric on the 91 cm Fourdrinier paper machine was a design 463 Monoflex JDL 145×120 mesh double layer with: forming Board, three 7.6 cm diameter table rolls, five foil boxes with four foils each, four flat boxes with adjustable vacuum.

Paper property (e.g. tensile strength, tear strength, burst strength) improvements obtained from the 1% solubilized collagen additions (Table 4B). For the mixed fiber stocks, machine direction tensile strength improvements were in the range of 25–30% while improvements in the 100% old corrugated containers and old newsprint stocks were in the range of 15–20%.

Biological oxygen demand (BOD) effects from the addition of the solubilized collagen to the mixed fiber were essentially improved over the plain fiber papers themselves, indicating increased retention of paper solids when solubilized collagen was added.

Surface pH measurements of all the papers produced during the trials were acidic even though the water at the papermaking facilities averaged pH 7 for the month of January, which is typical for the water supply. The solubilized collagen-containing papers showed somewhat lower pHs (more acidic) than the other papers. For some eventual end-use applications, it may eventually be desirable to bring the pHs of the solubilized collagen-containing papers to a more neutral level, after the papers have been formed.

TABLE 3B

Properties of Control Papers from Example No. 3B[1]

| Sample No. | Paper Identification | pH | BW | Tensile St. MD | Tensile St. CD | TS/BW | Tear MD | Tear CD | Caliper | Mullen Burst | BOD |
|---|---|---|---|---|---|---|---|---|---|---|---|
| | | | | Control Papers | | | | | | | |
| 16A | 100% OCC | — | 14.2 | — | — | 1.68 | 71.3 | 76.1 | .10 | .189 | 380 |
| 19A | 75/25 OCC/ONP | — | — | — | — | 1.49* | — | — | — | .151 | — |
| 17CA | 50/50 OCC/ONP | — | 14.1 | — | — | 1.23 | 53.7 | 58.8 | .12 | .113 | 170 |
| 18A | 25/75 OCC/ONP | — | — | — | — | 1.08* | — | — | — | .105* | — |
| 15A | 100% ONP | — | 14.3 | — | — | .93 | 37.1 | 41.1 | .13 | .096 | 190 |

[1]Abbreviations and units are as follows: BW = Basis Wt., kg/279 m$^2$ (lbs./3000 ft$^2$) of paper; TS = Tensile Strength, MPA; MD = Machine Direction; CD = Cross Direction; Tear = Tear Strength, grams; Caliper, mm; Mullen Burst, MPa; BOD = Biological Oxygen Deman, mg/liter.
*Estimates used for comparison of additives in Table 4B.

TABLE 4B

Properties of Experimental Papers from Example No. 3B[1]

| Sample No. | Paper Identification | pH | BW | Tensile MD | Tensile CD | MD TS/BW | MD ΔTS/BW | Tear[2] MD | Tear[2] CD | Caliper | Mullen Burst[2] | BOD[2] |
|---|---|---|---|---|---|---|---|---|---|---|---|---|
| | | | | Experimental Papers with 1% solubilized collagen | | | | | | | | |
| 16 | 100% OCC | (3.9) | 13.3 | 25.79 | 11.9 | 1.94 | 15% | 54.0 (24%) | 71.4 (6%) | .10 | .170 (10%) | 260 32% |
| 19 | 75/25 OCC/ONP | (3.9) | 13.3 | 25.87 | 10.73 | 1.91 | 29% | 58.8 | 68.6 | .11 | .145 (4%) | — |
| 17C | 50/50 OCC/ONP | (3.9) | 13.9 | 22.52 | 11.02 | 1.62 | 32% | 56.4 5% | 60.0 2% | .12 | .133 18% | 160 6% |
| 18 | 25/75 OCC/ONP | (3.9) | 14.1 | 19.01 | 9.14 | 1.35 | 25% | 47.6 | 51.2 | .13 | .122 17% | — |
| 15 | 100% ONP | (3.9) | 14.2 | 15.49 | 8.08 | 1.09 | 18% | 37.6 1% | 40.8 (1%) | .13 | .111 16% | 150 21% |

[1]Abbreviations and units are as follows: BW = Basis Wt., kg/279 m$^2$ (lbs./3000 ft$^2$) of paper; TS = Tensile Strength; MPa; MD = Machine Directoin; CD = Cross Direction; Tear = Tear Strength, grams; Caliper, mm; Mullen Burst, MPA; BOD = Biological Oxygen Deman, mg/liter. Basis weight is the paper weight in kg/279 m$^2$ (lbs. per 3000 sq. ft.) of paper
[2]Percentage numbers shown in these columns indicate that the data from the experimental papers were increased/decreased from the data of the equivalent daily control papers.

Example 4B
Mixing of Soluble Collagen and Pulp Fiber Prior to Headbox

Seven aliquots of solubilized collagen samples, prepared as described in Example 8A and collected after 16 or 20 hours, were pooled to yield a collagen solution with approximately 3.5 mg collagen solids/ml and a viscosity of 1150 cps at 20 rpm. Aliquots of this solution were diluted either 8-, 4-, or 2-fold with distilled water, or used undiluted, to give a range of concentrations of approximately 0.44, 1.75 and 3.5 mg collagen solids/ml.

Pulp slurries were prepared from ONP and OCC paper stocks at 3% consistency by shredding the materials, soaking them in 1% NaOH overnight, rinsing the soaked solids in tap water, and pulping the rinsed solids in a Tappi disintegrator for 15 minutes.

The pulp slurry was heated on a hot plate with manual stirring to approximately 120°–125° F. An aliquot of the heated pulp slurry (183 g) was combined with an aliquot of one of the diluted collagen solutions (63 g), and the combined collagen-pulp slurry was stirred by a blade-type mixer for 15 min. The resulting consistency of the pulp in the slurry was about 2.2%. The collagen solids to pulp solids ratio for these experiments therefore were approximately 0.5%, 1%, 2% and 4%. The initial temperature of the pulp-collagen slurry was approximately 106° F. +/−3° F. (41° C. +/−2° C.), and this temperature decreased to approximately 95° F. by the end of the stirring period.

At the end of the mixing period, the collagen-pulp slurry was put in the headbox of the Nobel and Wood handsheet system and collected by drainage through a Duotex 162-DD-226 forming fabric. The formed sheet was wet pressed, then calendered between blotter paper with the calender gap set at 30 mils. The sheet was then dried on a hot plate under tension for 1 min. Handsheets were equilibrated overnight in a controlled environment room (72° F./50% RH), then evaluated for basis weight (BW) and tensile strength (TS). Three sheets were prepared and tested for each sample condition. Results are summarized in Table 5B.

This example illustrates that increasing concentrations of dissolved collagen, when added to constant amounts of secondary pulp fiber, generally results in increases in tensile strength of sheets formed from the combination. The only exception in the data of Table 4B was for the OCC sheets with 0.5% added collagen, which yielded a corrected average Tensile Strength (TS/BW) slightly lower than the

TABLE 5B

Summary of Handsheet Properties for Example 4B Tests

| Pulp | Collagen Added % | Avg. BW* (lb/3000 ft²) | Avg. TS* | Avg. TS/BW* | ΔTS (%) |
|---|---|---|---|---|---|
| OCC | 0** | 31.0 | 1330 | 42.9 | — |
| OCC | 0.5 | 36.3 | 1430 | 39.4 | −8.1 |
| OCC | 1 | 35.2 | 1790 | 50.9 | +19 |
| OCC | 2 | 34.9 | 1840 | 52.7 | +23 |
| OCC | 4 | 35.7 | 1930 | 54.1 | +26 |
| ONP | 0** | 28.0 | 1370 | 48.9 | — |
| ONP | 0.5 | 32.7 | 1740 | 53.2 | +8.8 |
| ONP | 1 | 33.2 | 1930 | 58.1 | +19 |
| ONP | 2 | 31.8 | 2020 | 63.5 | +30 |
| ONP | 4 | 34.1 | 2400 | 70.4 | +44 |

*Average of 3 handsheets
**Control handsheets
BW = basis weight, lbs/3000 sq. ft. of paper;
TS = tensile strength OCC control Tensile Strength (−8.1%). This apparently inconsistent value is believed to have resulted from the consistently higher Basis Weights of the papers containing collagen (approximately 15% higher than control for the OCC sheets), which is believed to have resulted from the increased retention of pulp fines (small pulp fibers) in these samples. More fines, which would generally produce weaker papers, would tend to suppress the strength of the resulting paper, as in the 0.5%/OCC datum cited. This data clearly illustrates the general property of the collagen additive as a retention aid in paper formation.

As more collagen was added to either pulp slurry, the resulting paper strength increased, but the gain of strength was not linearly proportional to the amount of collagen added; the strength enhancement tended to decrease with increasing collagen/pulp ratio. This observation is consistent with a process of interaction of soluble collagen molecules with pulp fibers that results in saturation of the fiber surfaces with adsorbed collagen molecules. The strength enhancement observed in this binding [process is believed to result from inter-fiber bridges formed by soluble collagen molecules; saturation of the fiber surfaces with bound collagen would tend to limit the extent of such inter-fiber bridges, and thereby limit the maximum strength enhancement imparted by this process.

In the example cited, the apparent saturation process observed is interpreted as confirmation that interactions between soluble collagen molecules and pulp fiber surfaces is the predominate mechanism of strength enhancement, as opposed to the directly additive strength enhancement behavior that would be anticipated if these were no interactions between two populations of insoluble fibers mixed int he same proportions. In the examples summarized in Table 5B, the OCC fibers appeared to saturate at a lower collagen-to-pulp-solids ratio than did the ONP fibers.

This example also illustrates that the strength enhancement due to interactions between soluble collagen and pulp fibers can occur at temperatures above 40° C., above which collagen molecules would generally be expected to denature thermally. Previous citations have indicated that collagen addition to paper must be made below this denaturation temperature (G. Sauret et al, Le collagne ans la fabrication du papier, Revue A.T.P.L, Vol 33, No. 8, October 1979, pp 374–365). In a preliminary series of experiments (data not included herein), it was observed that if the pulp slurry and collagen solution were mixed at about 40° C. or above at low pulp slurry consistencies (e.g., 0.5% pulp solids), then the collagen tended to precipitate from solution before binding to the pulp fibers, leading to unsatisfactory (speckled) paper surfaces and no significant enhancement of tensile strength. On the other hand, if the pulp slurry and collagen solutions were mixed at higher pulp consistencies (e.g., 2.2% pulp solids as in Table 5B), the collagen does not precipitate and is successfully bound to the pulp fibers.

An additional example on the effect of temperatures in excess of 30° on collagen preparation is provided by the following example. USDA ground limed splits (0.06 inch cutting head) were centrifuged at 4° C. for 20 minutes at 10,000×g and the supernatant liquid was removed. The centrifuged limed splits were added in 7.5 g portions to two 1 L Erlenmeyer flasks that each contained deionized water 750 mL). The suspensions were stirred with a magnetic stirrer (2 inch stir bar), the pH was adjusted to pH 2.1 using concentrated hydrochloric acid, and 0.19 g pepsin was added to each flask. One flask was stirred at 19° C. and the other flask was stirred at 32° C. After 60 hours, the pH of the flasks were adjusted to Proximately 3.5 and the viscosities were measured at 20 rpm. The viscosity of the 19° C. reaction was 620 cps and the viscosity of the 32° C. reaction was 10 cps.

Both collagen preparations were added to pulp (collagen is approximately 1% of pulp) and the ability of these preparations to improve the properties of paper were measured. The preparation made at 19° provided no tensile strength/basis weight enhancement.

This shows that completely hydrolyzed soluble collagen does not appear to contribute to enhancement of tensile strength. The measurement of viscosity below about 20 cps does not appear sufficient to predict the degree of strength enhancement of paper mode with these solutions.

While the various examples above have focused on papermaking the invention could also be used in the making of various products such as molded products or paperboard where a cellulosic pulp can be bonded by solubilized collagen.

Various types of water such as Columbus, Ohio tap water; Savannah, Ga. tap water; whitewater from the papermaking process; and whitewater reduced in solids content were used; thus, it appears that the type of water is not critical in the invention for either the collagen making process or the papermaking process and a wide latitude for water supplies is possible.

While the forms of the invention herein disclosed constitute presently preferred embodiments, many others are possible. It is not intended herein to mention all of the possible equivalent forms or ramifications of the invention. It is to be understood that the terms used herein are merely descriptive, rather than limiting, and that various changes may be made without departing from the spirit of the scope of the invention.

We claim:

1. A method for making a collagen strengthened cellulosic sheet comprising:
   a. providing a cellulosic pulp slurry;
   b. adding solubilized collagen having a number average molecular weight above 300,000 daltons to said pulp slurry, and mixing for a time effective for interaction of said cellulosic pulp slurry and solubilized collagen;
   c. forming said interacted cellulosic pulp slurry and solubilized collagen into a sheet; and
   d. drying said sheet.

2. The method of claim 1 wherein said sheet is a paper sheet.

3. A method for using solubilized collagen having a number average molecular weight above 300,000 daltons for strengthening paper comprising:
   mixing said solubilized collagen with a cellulosic pulp slurry;
   molding said mixture and drying.

4. A method for making a collagen strengthened cellulosic sheet comprising:
   a. mixing a cellulosic material selected from the group consisting of virgin paper pulp, broke, reclaimed newsprint, reclaimed carton container, or a mixture thereof with a solution comprising water, or water and caustic, and mechanically pulping until a pulp slurry is formed having a consistency of about 3 wt % to about 6 wt % based on dry pulp solids;
   b. diluting said pulp slurry to a consistency of about 1 wt % to about 3 wt % based on dry pulp solids and adjusting pH to about 3.5 to about 7.0;
   c. adding between about 0.1 dry wt % to about 2 dry wt % soluble collagen having a number average molecular weight above 300,000 daltons (based on dry weight of cellulosic material) to said diluted pulp slurry, and mixing at a shear rate and a time effective for interaction of said diluted pulp slurry solids and soluble collagen, whereby at least a substantial portion of said soluble collagen is bound to said paper pulp to form a collagen-pulp slurry;
   d. diluting said collagen-pulp slurry to between about 0.1 dry wt % and 1 dry wt % consistency;
   e. forming said collagen-pulp slurry into a sheet; and
   f. drying said sheet.

5. The method of claim 4, whereby said mixing in Step c is for at least 15 minutes.

6. The method of claim 4, whereby said pH is adjusted with an acid selected from the group consisting of muriatic acid, HCl, $HNO_3$, $H_2SO_4$, and acetic acid.

7. The method of claim 4, including an additional Step of coating said sheet of Step e with sizing prior to drying.

8. The method of claim 7 wherein said sizing further comprises: collagen hydrolyzate having a number average molecular weight of 100,000 daltons or less.

9. The method of claim 4, further comprising calendering said dried sheet.

10. The method of claim 4, whereby said NaOH solution in Step a has a concentration of about 0.25 wt % to about 1.00 wt % based on dry weight of solids and a pH range 10-14.

11. The method of claim 4, whereby said solubilized collagen has a number average molecular weight above 1,000,000 daltons.

12. The method of claim 4, whereby said mixing is at a shear rate adapted to promote collagen-pulp interactions without denaturation of the collagen triple helical structure.

13. The method of claim 4, whereby said collagen-paper slurry has a consistency of about 0.5 dry wt %.

14. The method of claim 4, whereby an alum/rosin additive is added after pulping in Step a or after dilution in Step b.

15. The method of claim 4, whereby after forming the sheet in Step e, said formed sheet is wet pressed to a preselected thickness prior to drying.

16. The method of claim 4, further comprising when only water is selected in Step a, the additional step of:
   a1. refining said pulp/water slurry from Step a, to fibrillate cellulose fibers in said slurry to obtain a degree of freeness that obtains a selected water drainage when forming a sheet in Step e.

17. The method of claim 16, whereby, when substantially reclaimed newsprint is selected, the degree of freeness is between about 100 CSF and about 150 CSF and when substantially reclaimed carton container is selected the degree of freeness is between about 300 CSF and about 400 CSF.

18. The method of claim 16, whereby an alum/rosin additive is added after refining in Step a1.

19. A method for making a collagen strengthened cellulosic sheet comprising:
   a. providing a cellulosic pulp slurry;
   b. adding solubilized collagen having a number average molecular weight above 300,000 daltons to said pulp slurry whereby said cellulosic pulp and said solubilized collagen have a consistency above about 2 wt %, and mixing for a time effective for interaction of said cellulosic pulp slurry and solubilized collagen and whereby said mixing is at a temperature above about 40° C.;
   c. forming said interacted cellulosic pulp slurry and solubilized collagen into a sheet; and
   d. drying said sheet.

20. A method for using soluble collagen in a paper making process comprising the steps of:
   a. providing a solution of soluble collagen having a number average molecular weight above 300,000 daltons;
   b. providing a cellulosic pulp slurry;
   c. mixing said soluble collagen with said cellulosic pulp slurry;
   d. using the mixture of Step c to produce a paper product of desired shape.

21. A method as set forth in claim 20, wherein said producing step comprises forming the mixture into a sheet.

22. A method as set forth in claim 20, wherein said producing step comprises molding the mixture into a desired shape.

23. A method as set forth in claim 20, wherein said cellulosic pulp slurry comprises cellulosic material selected from the group consisting of virgin paper pulp, broke, reclaimed newsprint, reclaimed carton container, or a mixture thereof.

24. A method as set forth in claim 20, whereby said mixing in Step c is conducted at a shear rate and at a time effective for interaction of said cellulosic pulp slurry and said soluble collagen.

25. A method as set forth in claim 24, whereby said shear rate is adapted to promote collagen/pulp interactions without denaturation of the collagen triple helical structure, and whereby at least a substantial portion of said soluble collagen is bound to said cellulosic pulp to form a collagen/pulp slurry.

26. A method as set forth in claim 24, whereby said time for mixing is at least about fifteen (15) minutes.

27. A method as set forth in claim 24, wherein said cellulosic pulp slurry is prepared by a method comprising:
   a. mixing cellulosic material selected from the group consisting of virgin paper pulp, broke, reclaimed newsprint, reclaimed carton container, or a mixture thereof, with a solution comprising water, or water and caustic; and
   b. pulping said mixture until a cellulosic pulp slurry is formed having a consistency of about 3 wt % to about 6 wt % based on dry pulp solids.

28. A method as set forth in claim 27, wherein said caustic comprises NaOH.

29. A method as set forth in claim 27, wherein said pulping step is mechanical.

30. A method as set forth in claim 27, further comprising diluting said slurry to a consistency of about 1 wt % to about 3 wt % dry pulp solids and adjusting pH to above about 3.5, preferably to about 7.

31. A method as set forth in claim 30, whereby said pH is adjusted with an acid selected from the group consisting of muriatic acid, HCl, $HNO_3$, $H_2SO_4$, and acetic acid.

32. A method as set forth in claim 20, wherein said soluble collagen is provided in the amount of about 0.1 dry wt % to about 2 dry wt % (based on dry weight of cellulosic material).

33. A method as set forth in claim 25, whereby said collagen/pulp slurry is diluted to a consistency of between about 0.1 dry wt % and 1 dry wt %.

34. A method as set forth in claim 20, further comprising drying the paper product produced from the mixture of said soluble collagen and said cellulosic pulp slurry.

35. A method as set forth in claim 21, further comprising calendaring said sheet.

36. A method as set forth in claim 21, further comprising wet pressing said sheet to a preselected thickness prior to drying.

37. A method as set forth in claim 20, wherein said soluble collagen has a number average molecular weight above about 1,000,000 daltons.

38. A method as set forth in claim 25, whereby said collagen/pulp slurry is diluted to a consistency of about 0.5 dry wt %.

39. A method as set forth in claim 28, whereby said NaOH has a concentration in solution of about 0.25 wt % to above about 1.00 wt % based on dry weight of solids and a pH range of about 10–14.

40. A method as set forth in claim 27, further comprising adding an internal sizing additive to said slurry after pulping.

41. A method as set forth in claim 40, wherein said internal sizing additive is an alum/rosin additive.

42. A method as set forth in claim 30, further comprising adding an internal sizing additive to said diluted slurry.

43. A method as set forth in claim 42, wherein said internal sizing additive is an alum/rosin additive.

44. A method as set forth in claim 27, further comprising: when only water is selected to mix with said cellulosic pulp slurry, refining said cellulosic pulp/water mixture to fibrillate cellulose fibers in said slurry to obtain a degree of freeness that effects a selected water drainage when forming a sheet.

45. A method as set forth in claim 44, whereby the degree of freeness is between about 100 CSF and about 150 CSF, when substantially reclaimed newsprint is selected as the cellulosic material.

46. A method as set forth in claim 44, whereby the degree of freeness is between about 300 CSF and about 400 CSF, when substantially reclaimed carton container is selected as the cellulosic material.

47. A method as set forth in claim 44, further comprising adding an internal sizing additive after said refining step.

48. A method as set forth in claim 47, wherein said internal sizing additive is an alum/rosin additive.

49. A method as set forth in claim 20, whereby said mixing in Step c is at a temperature above 40° C.

50. A method as set forth in claim 20, wherein said soluble collagen/cellulosic pulp mixture of Step c has a consistency above about 2 wt %.

* * * * *